(12) United States Patent
Chen et al.

(10) Patent No.: US 11,746,353 B2
(45) Date of Patent: Sep. 5, 2023

(54) SACCHAROMYCES CEREVISIAE STRAIN WITH HIGH YIELD OF ETHYL BUTYRATE AND CONSTRUCTION METHOD AND APPLICATION OF SACCHAROMYCES CEREVISIAE STRAIN

(71) Applicant: Tianjin University of Science and Technology, Tianjin (CN)

(72) Inventors: Yefu Chen, Tianjin (CN); Yanrui Ma, Tianjin (CN); Yongjing Du, Tianjin (CN); Sen Jiang, Tianjin (CN); Jinying Ren, Tianjin (CN); Guo Zhang, Tianjin (CN); Xinyue Kang, Tianjin (CN); Peng Zheng, Tianjin (CN); Xiaole Wu, Tianjin (CN); Dongguang Xiao, Tianjin (CN); Xuewu Guo, Tianjin (CN)

(73) Assignee: Tianjin University of Science and Technology, Tianjin (CN)

( * ) Notice: Subject to any disclaimer, the term of this patent is extended or adjusted under 35 U.S.C. 154(b) by 223 days.

(21) Appl. No.: 17/134,210

(22) Filed: Dec. 25, 2020

(65) Prior Publication Data
US 2021/0198679 A1 Jul. 1, 2021

(30) Foreign Application Priority Data
Dec. 27, 2019 (CN) .......................... 201911377295.3

(51) Int. Cl.
| | |
|---|---|
| C12N 15/81 | (2006.01) |
| C12G 3/021 | (2019.01) |
| C12N 9/04 | (2006.01) |
| C12N 9/02 | (2006.01) |
| C12N 9/10 | (2006.01) |
| C12N 9/88 | (2006.01) |
| C12P 7/62 | (2022.01) |

(52) U.S. Cl.
CPC ............. *C12N 15/81* (2013.01); *C12G 3/021* (2019.02); *C12N 9/001* (2013.01); *C12N 9/0006* (2013.01); *C12N 9/1029* (2013.01); *C12N 9/88* (2013.01); *C12P 7/62* (2013.01); *C12Y 101/01157* (2013.01); *C12Y 103/01038* (2013.01); *C12Y 103/01044* (2013.01); *C12Y 203/01009* (2013.01); *C12Y 402/01055* (2013.01)

(58) Field of Classification Search
None
See application file for complete search history.

(56) References Cited

U.S. PATENT DOCUMENTS

| | | | |
|---|---|---|---|
| 2009/0155874 A1* | 6/2009 | Clark | C12N 15/52 |
| | | | 435/254.11 |
| 2020/0165641 A1* | 5/2020 | Buck | C12N 15/8243 |

FOREIGN PATENT DOCUMENTS

| | | | | | |
|---|---|---|---|---|---|
| CN | 103409303 A | * | 11/2013 | | |
| CN | 105385615 A | * | 3/2016 | ............... | C12G 3/02 |
| CN | 105586282 A | | 5/2016 | | |
| CN | 106119140 A | * | 11/2016 | | |
| CN | 108085262 A | * | 5/2018 | ........... | C07K 14/395 |

OTHER PUBLICATIONS

Ma et al., Biosynthetic Pathway for Ethyl Butyrate Production in *Saccharomyces cerevisiae*, J. Agric. Food Chem 68, 2020, 4252-60. (Year: 2020).*
Layton et al., Engineering modular ester fermentative pathways in *Escherichia coli*, Metabolic Eng. 26, 2014, 77-88. (Year: 2014).*
Schadeweg et al., Increasing n-butanol production with *Saccharomyces cerevisiae* by optimizing acetyl-CoA synthesis, NADH levels and trans-2-enoyl-CoA reductase expression, Biotechnol. Biofuels 9, 2016, 257. (Year: 2016).*
Manikandan et al., Kinetic and Optimization Studies on Ethanol Production from Corn Flour, Engineering and Technology 37, 2010, 1010-13. (Year: 2010).*
Wiedemann et al., Codon-optimized bacterial gene improve L-arabinose fermentation in recombinant *Saccharomyces cerevisiae*. Appl Environ Microb 74, 2008, 2043-50. (Year: 2008).*
Wu et al., Engineering *Saccharomyces cerevisiae* for the production of the valuable monoterpene ester geranyl acetate, Microb. Cell Fact. 17, 2018, 85. (Year: 2018).*
Jordan et al., Hxt13, Hxt15, Hxt16 and Hxt17 from *Saccharomyces cerevisiae* representa novel type of polyol transporters, Sci. Reports 6, 2016, 23502. (Year: 2018).*
China Center of Industrial Culture Collection, CICC No. 32315, English.china-cicc.org, retrieved Jan. 27, 2023. (Year: 2023).*

* cited by examiner

*Primary Examiner* — Todd M Epstein
(74) *Attorney, Agent, or Firm* — Bayramoglu Law Offices LLC

(57) ABSTRACT

A *Saccharomyces cerevisiae* strain with high yield of ethyl butyrate and a construction method and an application thereof are provided. The strain is obtained by over-expressing in the starting strain acetyl coenzyme A acyl transferase gene Erg10, 3-hydroxybutyryl coenzyme A dehydrogenase gene Hbd, 3-hydroxybutyryl coenzyme A dehydratase gene Crt, trans-2-enoyl coenzyme A reductase gene Ter, and alcohol acyl transferase gene AAT. Compared to the starting bacteria not producing ethyl butyrate, the yield of ethyl butyrate of the constructed strain reaches 77.33±3.79 mg/L, the yield of the ethyl butyrate of the strain with double copy expression of gene Ter and gene AAT reaches 99.65±7.32 mg/L, increased by 28.9% compared with the EST strain, and 40.93±3.18 mg/L of ethyl crotonate is unexpectedly produced.

15 Claims, 13 Drawing Sheets
Specification includes a Sequence Listing.

SEQUENCE LISTING

<160> NUMBER OF SEQ ID NOS: 54

<210> SEQ ID NO 1
<211> LENGTH: 1197
<212> TYPE: DNA
<213> ORGANISM: Saccharomyces cerevisiae
<220> FEATURE:
<221> NAME/KEY: misc_feature
<223> OTHER INFORMATION: acetyl-CoA C-acetyltransferase gene Erg10

<400> SEQUENCE: 1

```
atgtctcaga acgtttacat tgtatcgact gccagaaccc caattggttc attccagggt      60
tctctatcct ccaagacagc agtggaattg ggtgctgttg ctttaaaagg cgccttggct     120
aaggttccag aattggatgc atccaaggat tttgacgaaa ttattttggg taacgttctt     180
tctgccaatt tgggccaagc tccggccaga caagttgctt tggctgccgg tttgagtaat     240
catatcgttg caagcacagt taacaaggtc tgtgcatccg ctatgaaggc aatcattttg     300
```

| | |
|---|---|
| ggtgctcaat ccatcaaatg tggtaatgct gatgttgtcg tagctggtgg ttgtgaatct | 360 |
| atgactaacg caccatacta catgccagca gcccgtgcgg gtgccaaatt tggccaaact | 420 |
| gttcttgttg atggtgtcga aagagatggg ttgaacgatg cgtacgatgg tctagccatg | 480 |
| ggtgtacacg cagaaaagtg tgcccgtgat tgggatatta ctagagaaca acaagacaat | 540 |
| tttgccatcg aatcctacca aaaatctcaa aaatctcaaa aggaaggtaa attcgacaat | 600 |
| gaaattgtac ctgttaccat taagggattt agaggtaagc ctgatactca agtcacgaag | 660 |
| gacgaggaac ctgctagatt acacgttgaa aaattgagat ctgcaaggac tgttttccaa | 720 |
| aaagaaaacg gtactgttac tgccgctaac gcttctccaa tcaacgatgg tgctgcagcc | 780 |
| gtcatcttgg tttccgaaaa agttttgaag gaaaagaatt tgaagccttt ggctattatc | 840 |
| aaaggttggg gtgaggccgc tcatcaacca gctgatttta catgggctcc atctcttgca | 900 |
| gttccaaagg ctttgaaaca tgctggcatc gaagacatca attctgttga ttactttgaa | 960 |
| ttcaatgaag cctttccggt tgtcggtttg gtgaacacta agattttgaa gctagaccca | 1020 |
| tctaaggtta atgtatatgg tggtgctgtt gctctaggtc acccattggg ttgttctggt | 1080 |
| gctagagtgg ttgttacact gctatccatc ttacagcaag aaggaggtaa gatcggtgtt | 1140 |
| gccgccattt gtaatggtgg tggtggtgct tcctctattg tcattgaaaa gatatga | 1197 |

<210> SEQ ID NO 2
<211> LENGTH: 849
<212> TYPE: DNA
<213> ORGANISM: Clostridium acetobutylicum
<220> FEATURE:
<221> NAME/KEY: misc_feature
<223> OTHER INFORMATION: 3-hydroxybutyryl-CoA dehydrogenase gene Hbd

<400> SEQUENCE: 2

| | |
|---|---|
| atgaaaaagg tatgtgttat aggtgcaggt actatgggtt caggaattgc tcaggcattt | 60 |
| gcagctaaag gatttgaagt agtattaaga gatattaaag atgaatttgt tgatagagga | 120 |
| ttagatttta tcaataaaaa tctttctaaa ttagttaaaa aggaaagat agaagaagct | 180 |
| actaaagttg aaatcttaac tagaatttcc ggaacagttg accttaatat ggcagctgat | 240 |
| tgcgatttag ttatagaagc agctgttgaa agaatggata ttaaaaagca gatttttgct | 300 |
| gacttagaca atatatgcaa gccagaaaca attcttgcat caaatacatc atcactttca | 360 |
| ataacagaag tggcatcagc aactaaaaga cctgataagg ttataggtat gcatttcttt | 420 |
| aatccagctc ctgttatgaa gcttgtagag gtaataagag gaatagctac atcacaagaa | 480 |
| acttttgatg cagttaaaga gacatctata gcaataggaa aagatcctgt agaagtagca | 540 |
| gaagcaccag gatttgttgt aaatagaata ttaataccaa tgattaatga agcagttggt | 600 |
| atattagcag aaggaatagc ttcagtagaa gacatagata agctatgaa acttggagct | 660 |
| aatcacccaa tgggaccatt agaattaggt gattttatag gtcttgatat atgtcttgct | 720 |
| ataatggatg ttttatactc agaaactgga gattctaagt atagaccaca tacattactt | 780 |
| aagaagtatg taagagcagg atggcttgga agaaaatcag gaaaaggttt ctacgattat | 840 |
| tcaaaataa | 849 |

<210> SEQ ID NO 3
<211> LENGTH: 786
<212> TYPE: DNA
<213> ORGANISM: Clostridium acetobutylicum
<220> FEATURE:
<221> NAME/KEY: misc_feature
<223> OTHER INFORMATION: 3-hydroxybutyryl-CoA dehydratase gene Crt

<400> SEQUENCE: 3

```
atggaactaa acaatgtcat ccttgaaaag gaaggtaaag ttgctgtagt taccattaac      60
agacctaaag cattaaatgc gttaaatagt gatacactaa agaaatgga ttatgttata     120
ggtgaaattg aaaatgatag cgaagtactt gcagtaattt taactggagc aggagaaaaa    180
tcatttgtag caggagcaga tatttctgag atgaaggaaa tgaataccat gaaggtaga    240
aaattcggga tacttggaaa taagtgtttt agaagattag aacttcttga aaagcctgta    300
atagcagctg ttaatggttt tgctttagga ggcggatgcg aaatagctat gtcttgtgat    360
ataagaatag cttcaagcaa cgcaagattt ggtcaaccag aagtaggtct cggaataaca    420
cctggttttg gtggtacaca aagactttca agattagttg gaatgggcat ggcaaagcag    480
cttatattta ctgcacaaaa tataaaggca gatgaagcat taagaatcgg acttgtaaat    540
aaggtagtag aacctagtga attaatgaat acagcaaaag aaattgcaaa caaaattgtg    600
agcaatgctc cagtagctgt taagttaagc aaacaggcta ttaatagagg aatgcagtgt    660
gatattgata ctgctttagc atttgaatca gaagcatttg gagaatgctt ttcaacagag    720
gatcaaaagg atgcaatgac agctttcata gagaaaagaa aaattgaagg cttcaaaaat    780
agatag                                                                786
```

<210> SEQ ID NO 4
<211> LENGTH: 1194
<212> TYPE: DNA
<213> ORGANISM: Treponema denticola
<220> FEATURE:
<221> NAME/KEY: misc_feature
<223> OTHER INFORMATION: trans-2-enoyl-CoA reductase gene Ter

<400> SEQUENCE: 4

```
atgattgtta agccaatggt tagaaacaac atttgtttga atgctcatcc acaaggttgc      60
aagaagggtg tcgaagacca gattgagtac actaagaaac gtattacagc tgaagtcaag    120
gctggtgcta aggctcctaa gaatgtttta gttttgggtt gttctaatgg ttacggtttg    180
gcatctagaa ttactgctgc tttcggttac ggagctgcta ctattggtgt ttcattcgaa    240
aaagctggtt cagaaacaaa atatggtaca cccggttggt ataataactt agcttttcgat    300
gaggctgcta gagggaagg tttgtactca gttacaattg atggtgatgc tttctctgat    360
gagattaagg ctcaagttat tgaagaagct aagaagaaag gtattaagtt cgatttaatt    420
gtctactcat tggcttctcc agttcgtact gatccagata ctggtataat gcataaatct    480
gtcttgaaac ctttttggtaa gacttttact ggtaaaactg tcgatccttt cactggtgaa    540
ttgaaagaaa tttctgctga acccgctaac gacgaggaag ctgctgctac agtcaaggtc    600
atgggtggtg aggattggga agatggatt aaacaattgt ctaaagaagg tttgttggaa    660
gaaggatgta ttacttttgc ttactcttac attggtcccg aagcaactca agctttgtac    720
agaaagggta caattggaaa ggctaaagag cacttggagg caactgcaca cagattgaat    780
aaagagaatc cttctattag agcatttgtt tctgttaata aggtttagt tacaagagct    840
tctgctgtca ttcccgttat tccattgtat ttagcatctt tattcaaagt tatgaaagaa    900
aaaggtaacc atgagggttg tattgaacaa attactagat tgtacgctga agattgtac    960
agaaaagatg gtactattcc agtcgatgaa gaaatagaa ttagaattga tgattgggaa   1020
ttggaagaag atgtccaaaa agcagtttct gctttgatgg aaaaggttac tggtgaaaat   1080
gctgaatctt taacagattt agctggttat agacatgatt tcttggcatc taatggtttc   1140
```

```
gatgttgaag gtattaatta cgaagctgaa gttgaaagat ttgatagaat ataa        1194
```

<210> SEQ ID NO 5
<211> LENGTH: 1359
<212> TYPE: DNA
<213> ORGANISM: Fragaria x ananassa
<220> FEATURE:
<221> NAME/KEY: misc_feature
<223> OTHER INFORMATION: alcohol acyltransferase gene AAT

<400> SEQUENCE: 5

```
atggaaaaaa ttgaagtctc tattaattca aaacatacaa ttaagccatc aacatcttca    60
acaccattgc agccatataa attgacttta ttggatcagt taactccacc agcttatgtt   120
ccaattgtct tcttttatcc aattacagat catgatttca atttgccaca gactttggct   180
gacttgagac aggctttgtc agaaacttta actttgtact atccattatc aggtagagtt   240
aaaaataatt tgtatataga cgatttcgaa gagggtgtcc catacttgga ggctagggtc   300
aactgcgaca tgactgattt tttgagatta agaaagattg aatgtttaaa cgaattcgtt   360
ccaataaaac cattttctat ggaagctata tctgatgaaa ggtatccatt attgggagtt   420
caagttaatg ttttttgattc aggtatagct attggtgttt ctgtttctca taagttgatt   480
gatggtggta cagctgattg ttttttgaag tcttggggtg ctgttttcag gggttgtagg   540
gaaaatatta ttcatccatc tttgtctgaa gcagcattgt tgttcccacc tagggatgac   600
ttgccagaaa aatatgttga tcaaatggaa gctttatggt tcgctggtaa gaaggtcgct   660
actagaaggt ttgtcttcgg tgttaaagct atttcttcta ttcaagacga ggctaagtct   720
gagtctgtcc ctaagccatc tagagtccac gcagttactg ttttttgtg gaaacattta   780
atagctgcat ctagagcttt gacatctggt acaacatcta ctagattgtc tattgcagct   840
caggctgtca acttgaggac tagaatgaac atggaaacag ttttagacaa cgcaactggt   900
aacttgtttt ggtgggctca ggcaattttg gaattgtctc acacaacacc tgaaatatct   960
gatttgaaat tatgtgattt ggttaacttg ttaaatggtt ctgttaagca atgtaacggt  1020
gattattttg aaactttaaa aggtaaggaa ggatacggta gaatgtgtga atatttagat  1080
ttccagagaa ctatgtcttc tatggagcca gcaccagata tttacttgtt ttcttcatgg  1140
acaaatttct ttaacccatt ggatttcggt tggggtagga catctggat tggtgttgct  1200
ggtaagattg agtctgcttc ttgcaaattc attatattgg tcccaacaca gtgcggttct  1260
ggtattgagg catgggtcaa tttggaggag gagaaaatgg ctatgttgga gcaggaccca  1320
cacttttttgg ctttggcttc accaaagaca ttgatttaa                        1359
```

<210> SEQ ID NO 6
<211> LENGTH: 1479
<212> TYPE: DNA
<213> ORGANISM: Saccharomyces cerevisiae
<220> FEATURE:
<221> NAME/KEY: misc_feature
<223> OTHER INFORMATION: strong promoter PGK1P

<400> SEQUENCE: 6

```
tctaactgat ctatccaaaa ctgaaaatta cattcttgat taggtttatc acaggcaaat    60
gtaatttgtg gtattttgcc gttcaaaatc tgtagaattt tctcattggt cacattacaa   120
cctgaaaata ctttatctac aatcatacca ttccttataac atgtccccctt aatactagga   180
tcaggcatga acgcatcaca gacaaaatct tcttgacaaa cgtcacaatt gatccctccc   240
```

| | |
|---|---|
| catccgttat cacaatgaca ggtgtcattt tgtgctctta tgggacgatc cttattaccg | 300 |
| ctttcatccg gtgatagacc gccacagagg ggcagagagc aatcatcacc tgcaaaccct | 360 |
| tctatacact cacatctacc agtgtacgaa ttgcattcag aaaactgttt gcattcaaaa | 420 |
| ataggtagca tacaattaaa acatggcggg cacgtatcat tgcccttatc ttgtgcagtt | 480 |
| agacgcgaat ttttcgaaga agtaccttca aagaatgggg tctcatcttg ttttgcaagt | 540 |
| accactgagc aggataataa tagaaatgat aatatactat agtagagata acgtcgatga | 600 |
| cttcccatac tgtaattgct tttagttgtg tattttagt gtgcaagttt ctgtaaatcg | 660 |
| attaatttt ttttctttcc tcttttatt aaccttaatt tttattttag attcctgact | 720 |
| tcaactcaag acgcacagat attataacat ctgcacaata ggcatttgca agaattactc | 780 |
| gtgagtaagg aaagagtgag gaactatcgc ataccctgcat ttaaagatgc cgatttgggc | 840 |
| gcgaatcctt tattttggct tcaccctcat actattatca gggccagaaa aggaagtgt | 900 |
| ttccctcctt cttgaattga tgttacccte ataaagcacg tggcctctta tcgagaaaga | 960 |
| aattaccgtc gctcgtgatt tgtttgcaaa aagaacaaaa ctgaaaaaac ccagacacgc | 1020 |
| tcgacttcct gtcttcctat tgattgcagc ttccaatttc gtcacacaac aaggtcctag | 1080 |
| cgacggctca caggttttgt aacaagcaat cgaaggttct ggaatggcgg gaagggtt | 1140 |
| agtaccacat gctatgatgc ccactgtgat ctccagagca agttcgttc gatcgtactg | 1200 |
| ttactctctc tctttcaaac agaattgtcc gaatcgtgtg acaacaacag cctgttctca | 1260 |
| cacactcttt tcttctaacc aaggggtgg tttagtttag tagaacctcg tgaaacttac | 1320 |
| atttacatat ataaaacttt gcataaattg gtcaatgcaa gaaatacata tttggtcttt | 1380 |
| tctaattcgt agttttttcaa gttcttagat gctttctttt tctcttttt acagatcatc | 1440 |
| aaggaagtaa ttatctactt tttacaacaa atataaaac | 1479 |

<210> SEQ ID NO 7
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 7

| | |
|---|---|
| aagatcggaa ttccagatct catgtctcag aacgtttaca ttg | 43 |

<210> SEQ ID NO 8
<211> LENGTH: 45
<212> TYPE: DNA
<213> ORGANISM: Artificial Sequence
<220> FEATURE:
<223> OTHER INFORMATION: The sequence is synthetized.

<400> SEQUENCE: 8

| | |
|---|---|
| gatctatcgc agatccctcg agtcatatct tttcaatgac aatag | 45 |

<210> SEQ ID NO 9
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 9

| | |
|---|---|
| aagatcggaa ttccagatct catgaaaaag gtatgtgtta tagg | 44 |

```
<210> SEQ ID NO 10
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 10
gatctatcgc agatccctcg agttattttg aataatcgta gaaacc          46

<210> SEQ ID NO 11
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 11
aagatcggaa ttccagatct catggaacta acaatgtca tcc               43

<210> SEQ ID NO 12
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 12
gatctatcgc agatccctcg agctatctat ttttgaagcc ttc              43

<210> SEQ ID NO 13
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 13
aagatcggaa ttccagatct catgattgtt aagccaatgg ttag             44

<210> SEQ ID NO 14
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 14
gatctatcgc agatccctcg agttatattc tatcaaatct ttc              43

<210> SEQ ID NO 15
<211> LENGTH: 41
<212> TYPE: DNA
<213> ORGANISM: Artificial Sequence
<220> FEATURE:
<223> OTHER INFORMATION: The sequence is synthetized.

<400> SEQUENCE: 15
aagatcggaa ttccagatct catggaaaaa attgaagtct c                41

<210> SEQ ID NO 16
<211> LENGTH: 46
<212> TYPE: DNA
<213> ORGANISM: Artificial Sequence
<220> FEATURE:
<223> OTHER INFORMATION: The sequence is synthetized.
```

```
<400> SEQUENCE: 16
gatctatcgc agatccctcg agttaaatca atgtctttgg tgaagc          46

<210> SEQ ID NO 17
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 17
gaagaatcct tacgcacata agc                                   23

<210> SEQ ID NO 18
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 18
cagttttgga tagatcagtt agactgagac attttgagta cgtc            44

<210> SEQ ID NO 19
<211> LENGTH: 42
<212> TYPE: DNA
<213> ORGANISM: Artificial Sequence
<220> FEATURE:
<223> OTHER INFORMATION: The sequence is synthetized.

<400> SEQUENCE: 19
gatccactag tggcctatgc gaaggaggta agatcggtgt tg              42

<210> SEQ ID NO 20
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 20
ggaacaggtg cttaacactc ac                                    22

<210> SEQ ID NO 21
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 21
ctatcctcca agacagcagt g                                     21

<210> SEQ ID NO 22
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 22
gtgtaacaac cactctagca cc                                    22

<210> SEQ ID NO 23
<211> LENGTH: 21
```

```
<212> TYPE: DNA
<213> ORGANISM: Artificial Sequence
<220> FEATURE:
<223> OTHER INFORMATION: The sequence is synthetized.

<400> SEQUENCE: 23
cagctgaagc ttcgtacgct g                                              21

<210> SEQ ID NO 24
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 24
gcataggcca ctagtggatc                                                20

<210> SEQ ID NO 25
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 25
ccatagagag aaggagcaag c                                              21

<210> SEQ ID NO 26
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 26
cagttttgga tagatcagtt agacggttga gaccgaagat ctcttg                   46

<210> SEQ ID NO 27
<211> LENGTH: 45
<212> TYPE: DNA
<213> ORGANISM: Artificial Sequence
<220> FEATURE:
<223> OTHER INFORMATION: The sequence is synthetized.

<400> SEQUENCE: 27
gatccactag tggcctatgc ccgttagcaa tatctcgcat tatag                    45

<210> SEQ ID NO 28
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 28
catgctacct tccatggttg ag                                             22

<210> SEQ ID NO 29
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 29
```

```
ggaattgctc aggcatttgc ag                                              22

<210> SEQ ID NO 30
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 30
gtggtctata cttagaatct ccag                                            24

<210> SEQ ID NO 31
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 31
gtagcaggag cagatatttc tg                                              22

<210> SEQ ID NO 32
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 32
ctatgaaagc tgtcattgca tcc                                             23

<210> SEQ ID NO 33
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 33
gatgtgccta tgaatatgca gc                                              22

<210> SEQ ID NO 34
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 34
cagttttgga tagatcagtt agactggtga ggactgttcg cttg                      44

<210> SEQ ID NO 35
<211> LENGTH: 41
<212> TYPE: DNA
<213> ORGANISM: Artificial Sequence
<220> FEATURE:
<223> OTHER INFORMATION: The sequence is synthetized.

<400> SEQUENCE: 35
gatccactag tggcctatgc ccaaggagag gagcttcttc c                         41

<210> SEQ ID NO 36
<211> LENGTH: 23
<212> TYPE: DNA
<213> ORGANISM: Artificial Sequence
```

```
<220> FEATURE:
<223> OTHER INFORMATION: The sequence is synthetized.

<400> SEQUENCE: 36
ggaatggtac agtgttacgt tcc                                          23

<210> SEQ ID NO 37
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 37
cgtattacag ctgaagtcaa ggc                                          23

<210> SEQ ID NO 38
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 38
ctgtgtgcag ttgcctccaa g                                            21

<210> SEQ ID NO 39
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 39
ggatcagtta actccaccag c                                            21

<210> SEQ ID NO 40
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 40
gcctcaatac cagaaccgca c                                            21

<210> SEQ ID NO 41
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 41
gctgtgtatg aagaattagt tcacg                                        25

<210> SEQ ID NO 42
<211> LENGTH: 45
<212> TYPE: DNA
<213> ORGANISM: Artificial Sequence
<220> FEATURE:
<223> OTHER INFORMATION: The sequence is synthetized.

<400> SEQUENCE: 42
cagttttgga tagatcagtt agaccatgac agagatcatc cttgg                  45
```

```
<210> SEQ ID NO 43
<211> LENGTH: 41
<212> TYPE: DNA
<213> ORGANISM: Artificial Sequence
<220> FEATURE:
<223> OTHER INFORMATION: The sequence is synthetized.

<400> SEQUENCE: 43
gatccactag tggcctatgc gagacatact tccttcaccg g          41

<210> SEQ ID NO 44
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 44
ccttgagcga tatctggaga ttg                              23

<210> SEQ ID NO 45
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 45
gccttgatca acaatgcaat cc                               22

<210> SEQ ID NO 46
<211> LENGTH: 45
<212> TYPE: DNA
<213> ORGANISM: Artificial Sequence
<220> FEATURE:
<223> OTHER INFORMATION: The sequence is synthetized.

<400> SEQUENCE: 46
cagttttgga tagatcagtt agagtgactg agcgcataat attcc      45

<210> SEQ ID NO 47
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 47
gatccactag tggcctatgc ctgagaagtc agaagatcca atc        43

<210> SEQ ID NO 48
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 48
gcaggtcttg ataatgatag agg                              23

<210> SEQ ID NO 49
<211> LENGTH: 23
<212> TYPE: DNA
<213> ORGANISM: Artificial Sequence
<220> FEATURE:
<223> OTHER INFORMATION: The sequence is synthetized.
```

<400> SEQUENCE: 49
tctaactgat ctatccaaaa ctg                                    23

<210> SEQ ID NO 50
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 50
cagcgtacga agcttcagct gtaacgaacg cagaattttc gag              43

<210> SEQ ID NO 51
<211> LENGTH: 1308
<212> TYPE: DNA
<213> ORGANISM: Saccharomyces cerevisiae
<220> FEATURE:
<221> NAME/KEY: misc_feature
<223> OTHER INFORMATION: gene GAL80

<400> SEQUENCE: 51
atggactaca acaagagatc ttcggtctca accgtgccta atgcagctcc cataagagtc      60
ggattcgtcg gtctcaacgc agccaaagga tgggcaatca agacacatta ccccgccata     120
ctgcaactat cgtcacaatt tcaaatcact gccttataca gtccaaaaat tgagacttct     180
attgccacca ttcagcgtct aaaattgagt aatgccactg cttttcccac tttagagtca     240
tttgcatcat cttccactat agatatgata gtgatagcta tccaagtggc cagccattat     300
gaagttgtta tgcctctctt ggaattctcc aaaaataatc cgaacctcaa gtatctttc     360 gtagaatggg cccttgcatg ttcactagat caagccgaat ccatttataa ggctgctgct     420
gaacgtgggg ttcaaaccat catctcttta caaggtcgta aatcaccata tattttgaga     480
gcaaaagaat taatatctca aggctatatc ggcgacatta ttcgatcga gattgctgga     540 aatggcggtt ggtacggcta cgaaaggcct gttaaatcac caaaatacat ctatgaaatc     600
gggaacggtg tagatctggt aaccacaaca tttggtcaca caatcgatat tttacaatac     660
atgacaagtt cgtactttc caggataaat gcaatggttt tcaataatat tccagagcaa     720
gagctgatag atgagcgtgg taaccgattg gccagcgag tcccaaagac agtaccggat     780 catctttat tccaaggcac attgttaaat ggcaatgttc cagtgtcatg cagtttcaaa     840
ggtggcaaac ctaccaaaaa atttaccaaa aatttggtca ttgacattca cggtaccaag     900
ggagatttga acttgaagg cgatgccggc ttcgcagaaa tttcaaatct ggtcctttac     960
tacagtggaa ctagagcaaa cgacttcccg ctagccaatg acaacaagc tcctttagac    1020 ccggggtatg atgcaggtaa agaaatcatg gaagtatatc atttacgaaa ttataatgcc    1080
attgtgggta atattcatcg actgtatcaa tctatctctg acttccactt caatacaaag    1140
aaaattcctg aattaccctc acaatttgta atgcaaggtt cgatttcga aggctttccc    1200 accttgatgg atgctctgat attacacagg ttaatcgaga gcgtttataa agtaacatg    1260 atgggctcca cattaaacgt tagcaatatc tcgcattata gtttataa              1308

<210> SEQ ID NO 52
<211> LENGTH: 1704
<212> TYPE: DNA
<213> ORGANISM: Saccharomyces cerevisiae
<220> FEATURE:
<221> NAME/KEY: misc_feature
<223> OTHER INFORMATION: gene HXT16

<400> SEQUENCE: 52

| | | |
|---|---|---|
| atggcaagcg aacagtcctc accagaaatt aatgcagata atctaaacag tagtgcagct | 60 |
| gacgttcatg tacagccacc cggagagaaa gaatggtcag acgggtttta tgacaaagaa | 120 |
| gtcattaatg gaaatacgcc agacgcaccg aagagaggct ttttaggtta ccttattatc | 180 |
| tacttactat gctatcctgt atcctttggc ggttttttac ctggttggga tagtggtatt | 240 |
| actgcaggct tcatcaatat ggataacttt aaaatgaatt ttggttctta caagcacagt | 300 |
| actggtgagt attatttgag caacgtgcgt atgggtcttc tcgtggccat gttcagtgta | 360 |
| ggatgttcca ttggcggtgt tgcttttgcg agacttgctg atactttagg tagaaggcta | 420 |
| gcaattgtaa tcgtggtttt ggtatatatg gttggtgcaa ttattcagat cagttcgaat | 480 |
| cacaaatggt accaatactt tgtcggtaag atcatctacg gtcttggtgc tggtggctgt | 540 |
| tcggtgttgt gtccaatgct tttatctgaa atagccccca cagatttgag aggtggactt | 600 |
| gtctcattgt accaacttaa catgaccttc ggtatttttct tgggttattg tagcgtttat | 660 |
| ggaacaagga agtatagtaa tactgcgcaa tggaggattc ctgtgggact atgctttctg | 720 |
| tgggctctaa ttatcatcgt tggcatgtta ttagttccag agtccccaag atatctgatt | 780 |
| gaatgtgaga gacatgaaga ggcctgtgtc tccatcgcca agatcgacaa ggtttcacca | 840 |
| gaggatccat gggtactcaa acaggctgat gaaatcaacg ccggtgtcct tgcccaaaga | 900 |
| gaactagggg aagcctcatg gaaagaactt ttctccgtca aaacaaaagt ccttcaacgt | 960 |
| ttgatcacag gtattcttgt gcaaaccttt ttgcaactta ctggtgaaaa ctacttcttc | 1020 |
| ttctacggaa ctaccatttt caaatcagtt gggcttactg atgggtttga gacttcgatc | 1080 |
| gtcctaggta cagtgaattt cttctccact attattgctg ttatggtcgt agacaaaata | 1140 |
| ggccgtcgta atgtctgtt attcggagcg gcttcaatga tggcttgtat ggtcatattt | 1200 |
| gcaagtatcg gggtaaaatg tctttacccct catggccagg atggtccatc ctcgaaaggt | 1260 |
| gcaggtaatg ccatgattgt gttcacatgc ttctatatat tctgctttgc aacgacatgg | 1320 |
| gcccctgttg cttatattgt ggttgccgag tcattcccctt cgaaggtcaa atctaaagca | 1380 |
| atgtcaattt cgactgcatt caactggtta tggcaattct tgattggttt tttcacacca | 1440 |
| ttcattactg ggtctatcca cttctattat ggttatgtgt tcgtaggttg tttggttgct | 1500 |
| atgttttttgt acgttttctt ctttttacca gaaacaattg gtctatcttt ggaggaaacc | 1560 |
| cagttactat atgaagaagg tataaaacca tggaaatctg catcttgggt accaccctca | 1620 |
| aggagaggag cttcttccag ggaaactgag gctaagaaga aaagctggaa agaagttttg | 1680 |
| aagttcccaa agagttttaa ttga | 1704 |

<210> SEQ ID NO 53
<211> LENGTH: 1809
<212> TYPE: DNA
<213> ORGANISM: Saccharomyces cerevisiae
<220> FEATURE:
<221> NAME/KEY: misc_feature
<223> OTHER INFORMATION: gene KU70

<400> SEQUENCE: 53

| | | |
|---|---|---|
| atgcgctcag tcactaatgc atttggcaat agtggagaac ttaacgatca agtggatgaa | 60 |
| acaggttata ggaagtttga tatccatgaa ggaattttgt tttgcattga actatcagag | 120 |
| acaatgttta aagagtcctc tgatctagag tataaatcac cattgttgga aattctggaa | 180 |

```
tcactagatg agctaatgtc acaattggtc ataacaagac ctgggacagc tattggttgc      240
tatttttatt actgtaacag agaggatgcc aaggaaggta tctatgaact ttttccatta      300
agggatataa atgctacatt tatgaagaaa ttgaacgatc ttttagaaga tttatcatcg      360
gggagaataa gcctatacga ctattttatg tttcaacaaa ctgggagtga aaagcaagtg      420
cgcttatctg tattattcac attcatgctt gacactttt tggaagagat tccgggtcaa       480
aagcaattaa gcaacaagag agtgttctta ttcactgaca ttgataaacc acaagaggcg      540
caagatatcg atgaacgggc aagattgaga aggcttacaa ttgatttatt tgataacaaa      600
gtgaattttg caactttttt tattggctat gccgataaac catttgacaa cgagttttat      660
tcggacatac tgcagttggg ttcacataca aatgagaata ctggtttgga ttctgaattt      720
gatggtccaa gtacaaagcc tatagatgct aaatacatca agtccagaat cctaaggaaa      780
aaggaggtaa agaggataat gtttcaatgt ccattaatct tggatgagaa acaaatttt      840 atagtcggag tcaagggtta cactatgtat acccatgaaa aagctggagt caggtataaa      900
cttgtttatg agcatgaaga tatcagacaa gaagcatatt caaaaagaaa attttaaat     960 cctataacag gagaagacgt tactggtaaa actgtcaagg tttatcctta tggtgaccatc    1020 gatatcaatc tatcagatag tcaagatcag atagtaatgg aggcttatac tcaaaaagat    1080 gcgttttga agattattgg gttccgttca tcgagcaaat cgatacacta tttcaataac     1140
atagacaaaa gttcgtttat cgtaccagat gaagcaaat atgaaggttc gataagaacc     1200
ttggcttctt tattaaaaat tttgagaaaa aagataaaa ttgcaatatt atgggggaag     1260
cttaaatcaa attcacatcc ttcactatat acgttatcac cctcaagcgt gaaggactac    1320
aacgaaggat tttatctcta cagggttcca ttcctagacg aaattcgaaa atttcctagt    1380
ttactatcct atgatgatgg ctctgaacat aaactagatt atgataacat gaaaaagta    1440 actcaaagta aatgggata ctttaacttg agggatggat ataacccatc cgatttcaaa    1500
aacccactat tacaaaaaca ttacaaagtt ttacatgatt acctgttgca aattgaaacc    1560
acttttgacg aaaatgagac acctaatact aaaaaagaca gaatgatgcg tgaggacgat    1620
tctttaagga aactatatta tatacgaaat aaaattttag aatctgagaa gtcagaagat    1680
ccaatcatcc aaaggctaaa taatatgtt aaaatctgga atatgttcta caaaaattt     1740 aacgatgata acatttcgat aaaagaagaa agaagccct tgataaaaaa gccgaaattc     1800
aatatataa                                                            1809
```

<210> SEQ ID NO 54  
<211> LENGTH: 825  
<212> TYPE: DNA  
<213> ORGANISM: Saccharomyces cerevisiae  
<220> FEATURE:  
<221> NAME/KEY: misc_feature  
<223> OTHER INFORMATION: gene LPP1

<400> SEQUENCE: 54

```
atgatctctg tcatggcgga tgagaaacat aaggagtatt ttaagctata ctactttcag      60
tacatgataa ttggtctatg tacgatatta ttcctctatt cggagatatc cctggtacct     120
aggggccaaa acatcgaatt tagtcttgat gaccccagta tatcaaaacg ttatgtacct     180
aacgaactcg tgggcccact agaatgtttg attttgagtg ttggactgag taacatggtc     240
gtcttctgga cctgcatgtt tgacaaggac ttactgaaga agaatagagt aaagagacta     300
agagagaggc cggacggaat ctcgaacgat tttcacttca tgcatactag cattctatgt     360
```

```
ctgatgctga ttataagcat aaatgctgcc ctaacaggcg ccttaaagtt gattatagga      420
aacttgaggc ctgactttgt tgatagatgt atacctgacc tccaaaagat gagtgattca      480
gattctttgg tttttggctt ggacatttgc aagcagacta acaaatggat tctatacgaa      540
ggcttaaaaa gcactccaag cggacattca agtttcatag tcagtaccat gggctttaca      600
tatctttggc aaagggtttt caccacacgc aatacaagaa gttgcatttg gtgcccttta      660
ttagctctag tagtaatggt ttcaaggggtt atcgatcaca gacatcattg gtacgatgtt     720
gtctctggag ctgttctagc atttttagtc atttattgtt gctggaaatg gacatttaca      780
aacttggcga aaagagacat acttccttca ccggttagtg tttag                     825
```

SACCHAROMYCES CEREVISIAE STRAIN WITH HIGH YIELD OF ETHYL BUTYRATE AND CONSTRUCTION METHOD AND APPLICATION OF SACCHAROMYCES CEREVISIAE STRAIN

CROSS REFERENCE TO THE RELATED APPLICATIONS

This application is based upon and claims priority to Chinese Patent Application No. 201911377295.3, filed on Dec. 27, 2019, the entire contents of which are incorporated herein by reference.

TECHNICAL FIELD

The invention belongs to the technical field of bioengineering, and particularly relates to a *Saccharomyces cerevisiae* strain capable of producing high-yield ethyl butyrate, and a construction method and application of the *Saccharomyces cerevisiae* strain.

SEQUENCE LISTING

The present application contains a Sequence Listing which has been submitted in ASCII format via EFS-Web and is hereby incorporated by reference in its entirety. Said ASCII copy is named 6-GBRSMJ012_sequence_listing_20201224-1015_ST25.txt, created Dec. 24, 2020, and 27,317 bytes in size.

BACKGROUND

The main components of Chinese Baijiu are water and ethanol which account for 97% to 98% of Baijiu, and the other flavor substances only account for 2% to 3%. However, with the continuous development of flavor chemistry, it is found that these flavor substances with little content determine the flavor and characteristics of Baijiu. Among numerous trace components, ester is the most important compound and has pleasant fruit flavor. A proper amount of ester can increase the flavor of wine. For Chinese Baijiu, ethyl acetate, ethyl hexanoate, ethyl lactate and ethyl butyrate are the four main aroma components of Chinese Baijiu, which directly determine the quality of Baijiu products. The ethyl butyrate, as one of the four aroma components of Baijiu, has an aroma similar to kiwi fruit and pineapples and is one of the Laojiao aroma components of Luzhou-flavor Baijiu. In addition, the ethyl butyrate is also widely applied to the formula of daily use chemical essence and edible essence and may be used to prepare essence with various fruit flavors and other flavors.

Although *Saccharomyces cerevisiae* has extremely high alcohol fermentation efficiency, it lacks corresponding acyl coenzyme and lacks alcohol acyltransferase, so the *Saccharomyces cerevisiae* has low ester-producing capacity Since 1960s, numerous enterprises have methods such as adding ester-producing *Saccharomyces* to co-ferment with the *Saccharomyces cerevisiae* or prolonging the fermentation period and cellaring time to improve the defects of insufficient aroma and weak aftertaste of Baijiu. However, by these methods, consumption of manpower and material resources is increased while the yield of ester is increased, the fermentation period is prolonged and unpleasant odor substances such as bran smell, acrid odor, sour smell and the like. In addition, the *Saccharomyces cerevisiae* is the core of the brewing industry, and its performance is directly related to the quality and production cost of wine.

In the fermentation process, the ethyl butyrate is mainly produced by butyric acid produced by butyric acid bacteria and ethanol produced by the *Saccharomyces cerevisiae* under the action of esterifying enzyme, and the *Saccharomyces cerevisiae* itself hardly produces the ethyl butyrate and has no metabolic pathway to produce the ethyl butyrate; therefore, it is impossible to directly use the *Saccharomyces cerevisiae* to produce the ethyl butyrate.

SUMMARY

An objective of the present invention is to solve the problem that the *Saccharomyces cerevisiae* does not synthesize the ethyl butyrate in wine production and provide a method for constructing a *Saccharomyces cerevisiae* strain capable of producing ethyl butyrate. Specifically, a butyryl coenzyme A (CoA) producing pathway is constructed in *Saccharomyces* to make the *Saccharomyces cerevisiae* to produce the butyryl coenzyme A; and based on this, high-efficiency alcohol acyltransferase is introduced into the *Saccharomyces cerevisiae*, thereby constructing a complete ethyl butyrate pathway and producing the ethyl butyrate. Further, the key enzyme gene in the production pathway of the ethyl butyrate is subjected to double-copy expression, so that the yield of the ethyl butyrate is greatly increased.

To solve the above problem, a first objective of the present invention is to provide a *Saccharomyces cerevisiae* gene engineering strain capable of producing high-yield ethyl butyrate. The strain is constructed by taking the *Saccharomyces cerevisiae* as a starting strain through overexpression of an acetyl-CoA C-acetyltransferase gene Erg10, 3-hydroxybutyryl-CoA dehydrogenase gene Hbd, 3-hydroxybutyryl-CoA dehydratase gene Crt, trans-2-enoyl-CoA reductase gene Ter and alcohol acyltransferase AAT at the same time.

Further, the gene Ter is subjected to single-copy expression or double-copy expression; and the gene AAT is subjected to single-copy expression or double-copy expression.

Further, the acetyl-CoA C-acetyltransferase gene Erg10 is derived from the *Saccharomyces cerevisiae*.

Further, in the acetyl-CoA C-acetyltransferase gene Erg10, the gene ID is 856079, and the nucleotide sequence is shown as SEQ ID NO:1 in a nucleotide sequence table.

Further, the 3-hydroxybutyryl-CoA dehydrogenase gene Hbd is derived from *Clostridium acetobutylicum*.

Further, in the 3-hydroxybutyryl-CoA dehydrogenase gene Hbd, the gene ID is 1118891, and the nucleotide sequence is shown as SEQ ID NO:2 in the nucleotide sequence table.

Further, the 3-hydroxybutyryl-CoA dehydratase gene Crt is derived from *Clostridium acetobutylicum*.

More preferably, in the 3-hydroxybutyryl-CoA dehydratase gene Crt, the gene ID is 1118895, and the nucleotide sequence is shown as SEQ ID NO:3 in the nucleotide sequence table.

Preferably, the trans-2-enoyl-CoA reductase gene Ter is derived from treponema.

Further, the gene ID of the trans-2-enoyl-CoA reductase gene Ter is 2741560, and the nucleotide sequence of the gene Ter optimized by a *Saccharomyces cerevisiae* codon is shown as SEQ ID NO:4 in the nucleotide sequence table.

Further, the alcohol acyltransferase gene AAT is derived from strawberry (the name published by NCBI is *Fragaria x ananassa*).

Further, the protein_ID of the alcohol acyltransferase gene AAT is AAG13130.1 and the nucleotide sequence of the gene AAT optimized by a *Saccharomyces cerevisiae* codon is shown as SEQ ID NO:5 in the nucleotide sequence table.

Further, the starting *Saccharomyces* strain is *Saccharomyces cerevisiae* CICC32315.

The overexpression of the acetyl-CoA C-acetyltransferase gene Erg10 aims to synthesize acetoacetyl-CoA by the acetyl-CoA.

The heterologous overexpression of the 3-hydroxybutyryl-CoA dehydrogenase gene Hbd aims to synthesize 3-hydroxybutyryl-CoA by the acetoacetyl-CoA.

The heterologous overexpression of the 3-hydroxybutyryl-CoA dehydratase gene Crt aims to synthesize crotonoyl-CoA by the 3-hydroxybutyryl-CoA.

The heterologous overexpression of the trans-2-enoyl-CoA reductase Ter aims to synthesize butyryl-CoA by the crotonoyl-CoA.

The heterologous overexpression of the alcohol acyltransferase gene AAT aims to introduce alcohol acyltransferase so as to construct a complete ethyl butyrate pathway and produce the ethyl butyrate.

At least one gene of the gene Ter or the gene AAT in the pathway is subjected to double-copy expression because the activity of Ter is far lower than the activity of other enzyme in the synthesis pathway of the butyryl-CoA and the key last step of ethyl butyrate synthesis through catalysis of AAT may limit the production of the ethyl butyrate. Therefore, the Ter and the AAT genes are subjected to double copy, thus obviously increasing the yield of the ethyl butyrate of the *Saccharomyces cerevisiae*.

A second objective of the present invention is to provide a method for constructing the *Saccharomyces cerevisiae* strain capable of producing high-yield ethyl butyrate. The acetyl-CoA C-acetyltransferase gene Erg10 is overexpressed by a strong promoter, meanwhile, the 3-hydroxybutyryl-CoA dehydrogenase gene Hbd and the 3-hydroxybutyryl-CoA dehydratase gene Crt are connected in series to jointly replace a gene GAL80, and the gene Hbd and the gene Crt are subjected to heterologous expression respectively by strong promoters; meanwhile, the trans-2-enoyl-CoA reductase gene Ter and the alcohol acyltransferase AAT are connected in series to jointly replace a gene HXT16, and the gene Ter and the gene AAT are subjected to heterologous expression respectively by strong promoters.

Further, at least one gene of the gene Ter and the gene AAT is subjected to double-copy expression.

Further, the double-copy heterologous expression of the treponema trans-2-enoyl-CoA reductase gene Ter is realized by replacing a gene LPP1 and through heterologous expression by the strong promoter.

Further, the double-copy heterologous expression of the alcohol acyltransferase AAT is realized by replacing a gene KU70 and through heterologous expression by the strong promoter.

Further, the strong promoter is $PGK1_P$.

The gene ID of the $PGK1_P$ is 850370, and the nucleotide sequence is shown as SEQ ID NO:6 in the nucleotide sequence table.

The gene GAL80, with the gene ID: 854954, is derived from the *Saccharomyces cerevisiae*. (shown as SEQ ID NO:51)

The gene HXT16, with the gene ID: 853623, is derived from the *Saccharomyces cerevisiae*. (shown as SEQ ID NO:52)

The gene KU70, with the gene ID: 855328, is derived from the *Saccharomyces cerevisiae*. (shown as SEQ ID NO:53)

The gene LPP1, with the gene ID: 852114, is derived from the *Saccharomyces cerevisiae*. (shown as SEQ ID NO:54)

Further, the method for constructing the *Saccharomyces cerevisiae* gene engineering strain capable of producing high-yield ethyl butyrate includes the following steps:

(1) taking a haploid of the *Saccharomyces cerevisiae* strain as a starting strain and the Erg10 as an integration site, sequentially connecting an upstream homologous arm FA of the gene Erg10, a PGK1p-Erg10-PGK1t segment, a gene KanMX and a downstream homologous arm FB of the gene Erg10 and inserting into the integration site, removing the gene KanMX by a pGAP plasmid after homologous recombination, and conducting subculture to obtain a recombinant strain not containing the pGAP plasmid;

(2) meanwhile, taking a gene GAL80 as an integration site, sequentially connecting an upstream homologous arm FA of the gene GAL80, a PGK1p-Hbd-PGK1t segment, the gene, the gene KanMX, a PGK1p-Crt-PGK1t segment and a downstream homologous arm FB of the gene GAL80 and inserting into the integration site, removing the gene KanMX by the pGAP plasmid after homologous recombination, and conducting subculture to obtain a recombinant strain not containing the pGAP plasmid; and (3) meanwhile, taking a gene HXT16 as an integration site, sequentially connecting an upstream homologous arm FA of the gene HXT16, a PGK1p-Ter-PGK1t segment, the gene, the gene KanMX, a PGK1p-AAT-PGK1t segment and a downstream homologous arm FB of the gene HXT16 and inserting into the integration site, removing the gene KanMX by the pGAP plasmid after homologous recombination, and conducting subculture to obtain a recombinant strain not containing the pGAP plasmid.

Further, in the step (1), the haploid of the *Saccharomyces cerevisiae* strain is an a haploid.

Further, the recombinant strain obtained by the construction method is subjected to double-copy construction of at least one gene of the gene Ter and the gene AAT More preferably, the double-copy construction of the gene Ter includes the following steps:

taking the recombinant strain obtained in the step (3) as a starting strain and an LPP1 gene as an integration site, sequentially connecting an upstream homologous arm FA of the gene LPP1, the PGK1p-Ter-PGK1t segment, the gene KanMX and a downstream homologous arm FB of the gene LPP1 and inserting into the integration site, removing the gene KanMX by the pGAP plasmid after homologous recombination, and conducting subculture to obtain a recombinant strain not containing the pGAP plasmid.

More preferably, the double-copy construction of the gene AAT includes the following steps: taking the recombinant strain obtained in the step (3) as a starting strain and a KU70 gene as an insertion site, sequentially connecting an upstream homologous arm FA of the gene KU70, the PGK1p-AAT-PGK1t segment, the gene KanMX and a downstream homologous arm FB of the gene KU70 and inserting into the integration site, removing the gene KanMX by the pGAP plasmid after homologous recombination, and conducting subculture to obtain a recombinant strain not containing the pGAP plasmid.

A third objective of the present invention is to provide application of the *Saccharomyces cerevisiae* strain capable of producing high-yield ethyl butyrate, preferably, the application of the *Saccharomyces cerevisiae* strain to production of high-yield ethyl butyrate in the fields of fermentation brewing, fermented food and essence and flavors.

Preferably, the fermentation steps of the *Saccharomyces cerevisiae* gene engineering strain are as follows:

after performing two-stage activation on the *Saccharomyces cerevisiae* gene engineering strain, inoculating seed liquid to a fermentation medium according to an inoculation amount of 8% to 12%, and performing static fermentation at 28° C. to 30° C. for 80 h to 86 h.

Weighing is conducted for one time every 12 h in the later stage of fermentation, and when the weight loss of two times is less than 1 g, the end of fermentation is determined.

Preferably, the fermentation medium consists of corn flour of 300-320 g/L, high-temperature resistant α-amylase of $(3-4)\times10^4$ U/L, saccharifying enzyme of 90-100 U/L, acid proteinase of 10-20 U/L, nutritive salt solution of 5.5-5.6 mL/L and the balance of water, wherein the nutritive salt solution consists of $MgSO_4$ of 140-160 g/L, $KH_2PO_4$ of 70-80 g/L, urea of 80-85 g/L and the balance of water.

Preferably, the two-stage activation condition of the *Saccharomyces cerevisiae* is as follows: firstly, inoculating the *Saccharomyces cerevisiae* gene engineering strain into a primary seed culture medium, performing static culture at 28° C. to 30° C. for 24 h to obtain primary seed liquid, inoculating the primary seed liquid into a secondary seed culture medium according to an inoculation amount of 8% to 12%, performing static culture at 28° C. to 30° C. until the later stage of a logarithmic phase, namely for 15 h to 18 h, to obtain secondary seed liquid.

More preferably, the primary seed culture medium consists of corn flour of 80-85 g/L, high-temperature resistant α-amylase with an adding amount being about $(0.5-1.0)\times10^4$ U/L, saccharifying enzyme with enzyme activity being about 30-35 U/L and the balance of water, wherein the sugar degree is 8°BX.

More preferably, the secondary seed culture medium consists of corn flour of about 120-130 g/L, high-temperature resistant α-amylase with an adding amount being about $(1.0-2.0)\times10^4$ U/L, saccharifying enzyme with enzyme activity being about 45-55 U/L and the balance of water, wherein Second level degree is 12°BX.

Beneficial Effects:

1. According to the technical content of the present invention, a new pathway is provided for regulating and controlling the flavor substances in wine products, and a *Saccharomyces cerevisiae* gene engineering strain capable of producing high-yield ethyl butyrate is constructed by introducing an exogenous butyryl coenzyme A synthesis pathway and introducing high-efficiency alcohol acyltransferase capable of synthesizing corresponding ethyl ester by acyl coenzyme and ethanol, so that the defect of uncoordinated flavor substances caused by inability to produce the ethyl butyrate by the common *Saccharomyces cerevisiae* is overcome, and the *Saccharomyces cerevisiae* can maintain excellent fermentation characteristic of alcohol while producing high-yield ethyl butyrate in the fermentation process. Compared with the wild *Saccharomyces cerevisiae* which cannot produce the ethyl butyrate, the strain has the advantages that the yield of the ethyl butyrate reaches 99.65±7.32 mg/L to achieve the aim of producing high-yield ethyl butyrate, ethyl crotonate of 40.93±3.18 mg/L (crotonoyl-CoA is a precursor of the butyryl coenzyme A) is produced, theoretical foundation is laid for brewing Baijiu with excellent flavor and beneficial to health, a wide market prospect is achieved, and it is of great significance in maintaining and strengthening the flavor characteristic of the Baijiu products, improving and stabilizing quality, even reforming the fermentation process.

2. The *Saccharomyces cerevisiae* capable of producing the ethyl butyrate according to the present invention provides a solution idea for solving the problem of uncoordinated ester in the Baijiu production on the premise of maintaining excellent fermentation performance, and has important market value.

DETAILED DESCRIPTION OF THE EMBODIMENTS

The present disclosure is described below through specific embodiments. Unless otherwise specified, the technical means used in the present disclosure are all methods known to those skilled in the art. In addition, the embodiments should be understood as illustrative, rather than limiting the scope of the disclosure, which is only limited by the scope of the claims. For those skilled in the art, without departing from the spirit and scope of the present disclosure, various changes or modifications to the material composition and amount used in these embodiments also belong to the protection scope of the present disclosure.

The *Saccharomyces cerevisiae* used in the present invention may adopt *Saccharomyces cerevisiae* strains from any source. The *Saccharomyces cerevisiae* strains used in the following embodiments are all a haploids (AY14-α) of *Saccharomyces cerevisiae* CICC32315.

Figure 1:
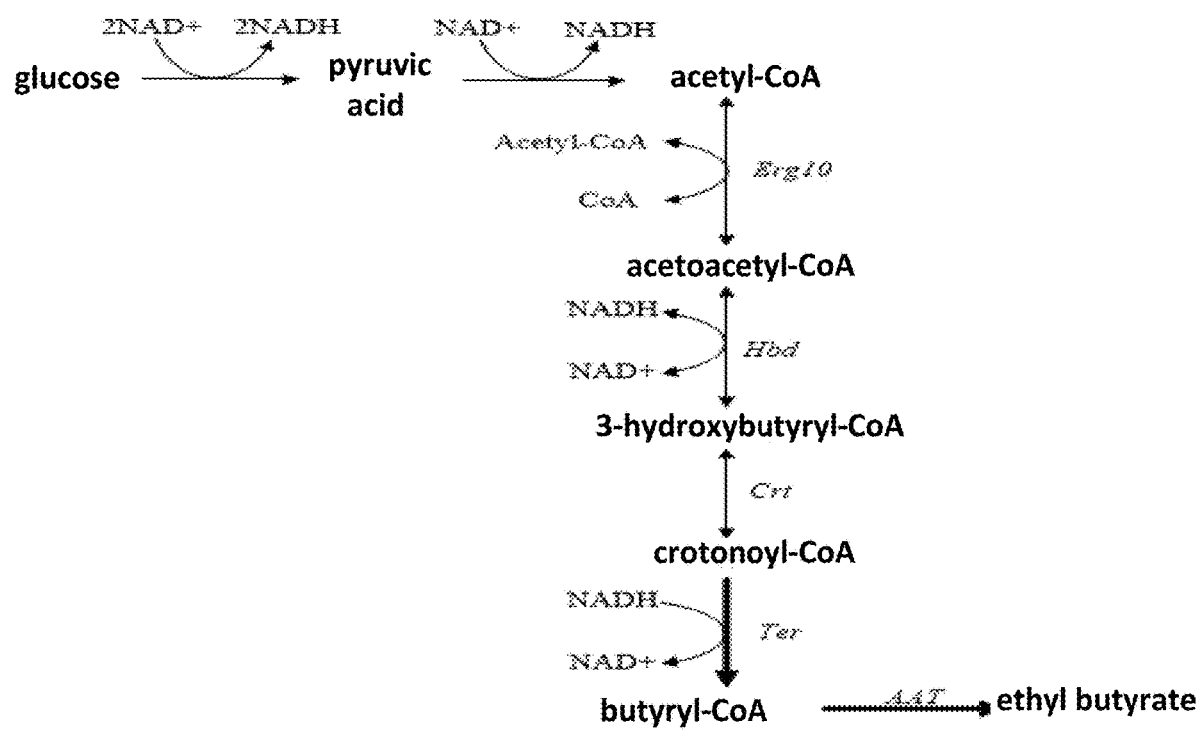
FIG. 1 is a metabolic diagram of an ethyl butyrate synthesis pathway constructed by *Saccharomyces cerevisiae*.

Firstly, the gene Erg10 of *Saccharomyces* was overexpressed (referring to FIG. 1), and 3-hydroxybutyryl-CoA dehydrogenase gene (Hbd) and 3-hydroxybutyryl-CoA dehydratase gene (Crt) derived from *Clostridium acetobutylicum* as well as trans-2-enoyl-CoA reductase gene (Ter) derived from treponema were subjected to heterologous expression in the *Saccharomyces cerevisiae* to construct a *Saccharomyces cerevisiae* strain ET with a butyryl coenzyme A producing pathway; secondly, a *Fragaria x ananassa* alcohol acyltransferase AAT was subjected to heterologous integration strong expression in the strain ET to obtain an ethyl butyrate-producing *Saccharomyces* strain EST; thirdly, the gene Ter and the gene AAT were subjected to double-copy expression respectively based on the strain EST to obtain a strain EDT capable of singly double-copying (dual-copying) the gene Ter and a strain EDS capable of singly double-copying the gene AAT. Finally, the AAT was subjected to double copy on the basis of the strain EDT capable of singly double-copying the gene Ter to obtain a strain EDST capable of double-copying the genes Ter and AAT simultaneously.

Embodiment 1: Construction of a *Saccharomyces cerevisiae* Strain Capable of Producing Ethyl Butyrate The embodiment adopts a starting strain CICC32315. The *Escherichia coli* DH5a is purchased from Takara company. The YPD culture medium is a universal complete culture medium, and the solid culture medium contains 2% (mass percentage) of imported agar powder.

According to each gene sequence and integration plasmid sequence in NCBI Genebank, the following primer is designed, as shown in Table 1.

TABLE 1

| Primers | | |
|---|---|---|
| Name of primer | Sequence (5'→3') | SEQ ID NO: |
| P-Erg10-U | AAGATCGGAATTCCAGATCTCATGTCT CAGAACGTTTACATTG | 7 |
| P-Erg10-D | GATCTATCGCAGATCCCTCGAGTCATA TCTTTTCAATGACAATAG | 8 |
| P-Hbd-U | AAGATCGGAATTCCAGATCTCATGAAA AAGGTATGTGTTATAGG | 9 |
| P-Hbd-D | GATCTATCGCAGATCCCTCGAGTTATTT TGAATAATCGTAGAAACC | 10 |
| P-Crt-U | AAGATCGGAATTCCAGATCTCATGGAA CTAAACAATGTCATCC | 11 |
| P-Crt-D | GATCTATCGCAGATCCCTCGAGCTATCT ATTTTTGAAGCCTTC | 12 |
| P-Ter-U | AAGATCGGAATTCCAGATCTCATGATTG TTAAGCCAATGGTTAG | 13 |
| P-Ter-D | GATCTATCGCAGATCCCTCGAGTTATAT TCTATCAAATCTTTC | 14 |
| P-AAT-U | AAGATCGGAATTCCAGATCTCATGGAA AAAATTGAAGTCTC | 15 |
| P-AAT-D | GATCTATCGCAGATCCCTCGAGTTAAAT CAATGTCTTTGGTGAAGC | 16 |

TABLE 1-continued

Primers

| Name of primer | Sequence (5'→3') | SEQ ID NO: |
|---|---|---|
| Erg10-FA-U | GAAGAATCCTTACGCACATAAGC | 17 |
| Erg10-FA-D | CAGTTTTGGATAGATCAGTTAGACTGAGACATTTTGAGTACGTC | 18 |
| Erg10-FB-U | GATCCACTAGTGGCCTATGCGAAGGAGGTAAGATCGGTGTTG | 19 |
| Erg10-FB-D | GGAACAGGTGCTTAACACTCAC | 20 |
| Erg10-U | CTATCCTCCAAGACAGCAGTG | 21 |
| Erg10-D | GTGTAACAACCACTCTAGCACC | 22 |
| KAN-U | CAGCTGAAGCTTCGTACGCTG | 23 |
| KAN-D | GCATAGGCCACTAGTGGATC | 24 |
| GAL80-FA-U | CCATAGAGAGAAGGAGCAAGC | 25 |
| GAL80-FA-D | CAGTTTTGGATAGATCAGTTAGACGGTGTAGACCGAAGATCTCTTG | 26 |
| GAL80-FB-U | GATCCACTAGTGGCCTATGCCCGTTAGCAATATCTCGCATTATAG | 27 |
| GAL80-FB-D | CATGCTACCTTCCATGGTTGAG | 28 |
| Hbd-U | GGAATTGCTCAGGCATTTGCAG | 29 |
| Hbd-D | GTGGTCTATACTTAGAATCTCCAG | 30 |
| Crt-U | GTAGCAGGAGCAGATATTTCTG | 31 |
| Crt-D | CTATGAAAGCTGTCATTGCATCC | 32 |
| HXT16-FA-U | GATGTGCCTATGAATATGCAGC | 33 |
| HXT16-FA-D | CAGTTTTGGATAGATCAGTTAGACTGGTGAGGACTGTTCGCTTG | 34 |
| HXT16-FB-U | GATCCACTAGTGGCCTATGCCCAAGGAGAGGAGCTTCTTCC | 35 |
| HXT16-FB-D | GGAATGGTACAGTGTTACGTTCC | 36 |
| Ter-U | CGTATTACAGCTGAAGTCAAGGC | 37 |
| Ter-D | CTGTGTGCAGTTGCCTCCAAG | 38 |
| AAT-U | GGATCAGTTAACTCCACCAGC | 39 |
| AAT-D | GCCTCAATACCAGAACCGCAC | 40 |
| LPP1-FA-U | GCTGTGTATGAAGAATTAGTTCACG | 41 |
| LPP1-FA-D | CAGTTTTGGATAGATCAGTTAGACCATGACAGAGATCATCCTTGG | 42 |
| LPP1-FB-U | GATCCACTAGTGGCCTATGCGAGACATACTTCCTTCACCGG | 43 |
| LPP1-FB-D | CCTTGAGCGATATCTGGAGATTG | 44 |
| KU70-FA-U | GCCTTGATCAACAATGCAATCC | 45 |
| KU70-FA-D | CAGTTTTGGATAGATCAGTTAGAGTGATCGAGCGCATAATATTCC | 46 |
| KU70-FB-U | GATCCACTAGTGGCCTATGCCTGAGAAGTCAGAAGATCCAATC | 47 |
| KU70-FB-D | GCAGGTCTTGATAATGATAGAGG | 48 |
| PGK1p-U | TCTAACTGATCTATCCAAAACTG | 49 |
| PGK1t-D | CAGCGTACGAAGCTTCAGCTGTAACGAACGCAGAATTTTCGAG | 50 |

The PCR amplification system used in the embodiment is shown in Table 2.

TABLE 2

PCR Amplification System

| Reaction System | Sample Adding Quantity |
|---|---|
| ddH$_2$O | Supplemented to 50 µL |
| 10× PCR Buffer | 5.0 µL |
| dNTP (0.2 m mol/L) | 4 µL |
| Upstream and downstream primers (10 m mol/L) | 1.5 µL for each one |
| Template: *Saccharomyces* total DNA | 1.0 µL |
| Taq DNA polymerase | 0.5 µL |

The main construction process of the strain is as follows:

(1) Construction of Yep352-PE/PH/PC/PT/PA Plasmid

Figure 2:
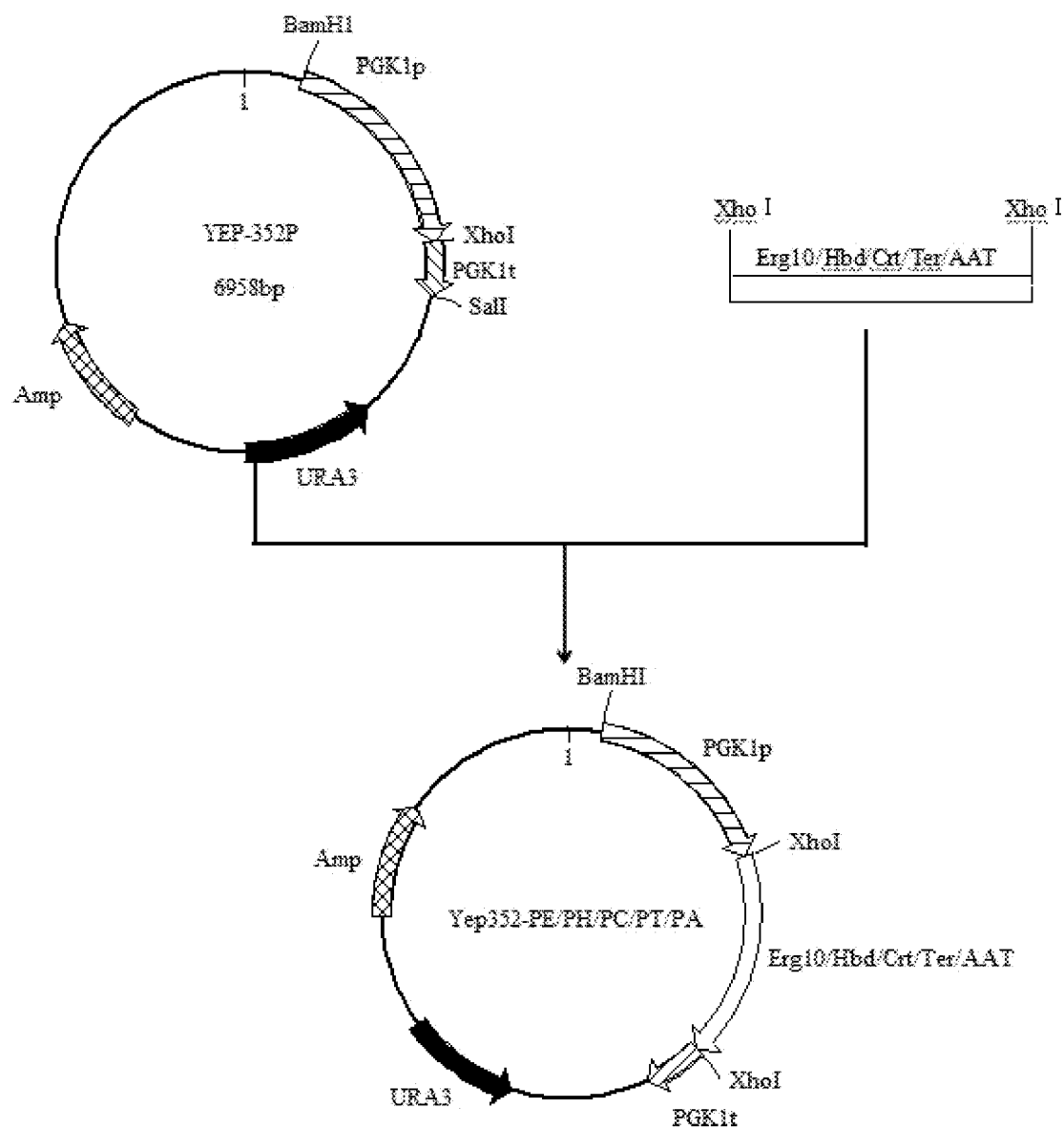
FIG. 2 is a schematic diagram of a construction process of recombinant plasmid Yep352-PE/PH/PC/PT/PA.
Figure 3A:
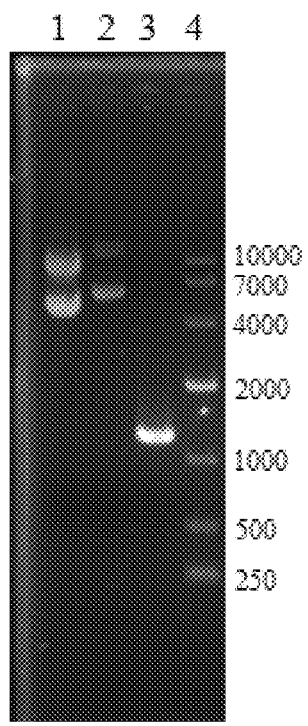
FIG. 3A is a verification electrophoretogram of construction of recombinant plasmid Yep352-PE, wherein lane 1 is a Yep352-P plasmid, lane 2 is Yep352-PE, lane 3 is an Erg10 gene segment, and lane 4 is a 10000 bp DNA Ladder Marker.
Figure 3B:
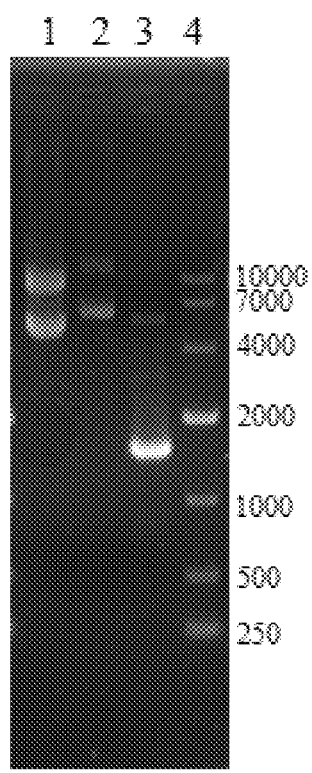
FIG. 3B is a verification electrophoretogram of construction of recombinant plasmid Yep352-PA, wherein lane 1 is a Yep352-P plasmid, lane 2 is Yep352-PA, lane 3 is an AAT gene segment, and lane 4 is a 10000 bp DNA Ladder Marker.
Figure 3C:
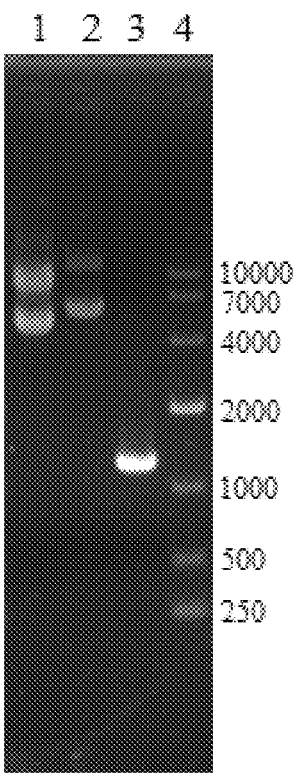
FIG. 3C is a verification electrophoretogram of construction of recombinant plasmid Yep352-PT, wherein lane 1 is a Yep352-P plasmid, lane 2 is Yep352-PT, lane 3 is a Ter gene segment, and lane 4 is a 10000 bp DNA Ladder Marker.
Figure 3D:
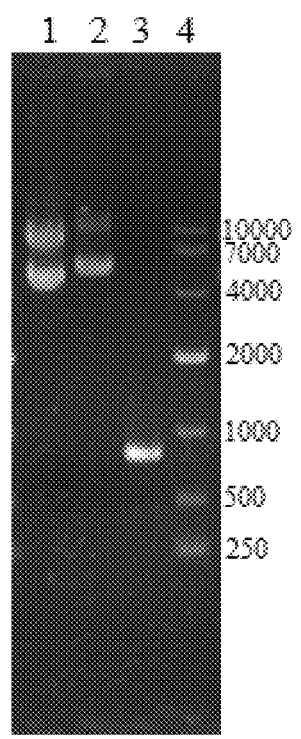
FIG. 3D is a verification electrophoretogram of construction of recombinant plasmid Yep352-PH, wherein lane 1 is a Yep352-P plasmid, lane 2 is Yep352-PH, lane 3 is a Hbd gene segment, and lane 4 is a 10000 bp DNA Ladder Marker.
Figure 3E:
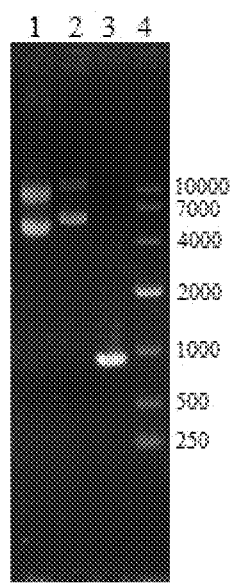
FIG. 3E is a verification electrophoretogram of construction of recombinant plasmid Yep352-PC, wherein lane 1 is a Yep352-P plasmid, lane 2 is Yep352-PC, lane 3 is a Crt gene segment, and lane 4 is a 10000 bp DNA Ladder Marker.

Recombinant plasmids carrying genes Erg10, Hbd, Crt, Ter and AAT were constructed by taking Yep352-P as a basic plasmid, short for recombinant plasmids Yep352-PE, Yep352-PH, Yep352-PC, Yep352-PT and Yep352-PA (short for Yep352-PE/PH/PC/PT/PA). The construction process is shown in FIG. 2, and the verification electrophoretogram is shown in FIG. 3A-E. By taking a haploid genome of the *Saccharomyces cerevisiae* CICC32315 as a template, PCR amplification was conducted by primer pairs P-Erg10-U (SEQ ID NO:7) and P-Erg10-D (SEQ ID NO:8) to obtain a 1197 bp Erg10 segment; PCR amplification was conducted by primer pairs P-Hbd-U (SEQ ID NO:9) and P-Hbd-D (SEQ ID NO:10) to obtain a 849 bp Hbd segment; PCR amplification was conducted by primer pairs P-Crt-U (SEQ ID NO:11) and P-Crt-D (SEQ ID NO:12) to obtain a 786 bp Crt segment; PCR amplification was conducted by primer pairs P-Ter-U (SEQ ID NO:13) and P-Ter-D (SEQ ID NO:14) to obtain a 1194 bp Ter segment; PCR amplification was conducted by primer pairs P-AAT-U (SEQ ID NO:15) and P-AAT-D (SEQ ID NO:16) to obtain a 1359 bp AAT segment; Yep352-P was subjected to enzyme cutting by restriction endonuclease Xho I, and the plasmid after enzyme cutting was respectively in recombinant connection to the five gene segments obtained by PCR by a lightening cloning kit to obtain recombinant plasmids Yep352-PE, Yep352-PH, Yep352-PC, Yep352-PT and Yep352-PA respectively.

The plasmid Yep352-P and the construction method thereof are derived from the patent *Saccharomyces cerevisiae* STRAIN CAPABLE OF PRODUCING HIGH-YIELD FLAVOR ETHYL ESTER AND CONSTRUCTION METHOD THEREOF with publication number CN105586282A. The Yep352-P plasmid is obtained by taking a plasmid pPGK1 as a template, amplifying a strong promoter segment PGK1p-PGK1t on the plasmid pPGK1 and connecting onto an expression vector Yep352.

(2) construction of a *Saccharomyces* strain capable of producing ethyl butyrate ① By taking the genome of CICC32315 *Saccharomyces* α haploid (hereinafter referred to as AY14-α) as a template, PCR amplification was conducted by primer pairs Erg10-FA-U (SEQ ID NO:17) and Erg10-FA-D (SEQ ID NO:18) to obtain an upper homologous arm Erg10-FA of an Erg10 site; PCR amplification was conducted by primer pairs Erg10-FB-U (SEQ ID NO:19) and Erg10-FB-D (SEQ ID NO:20) to obtain a lower homologous arm Erg10-FB of the Erg10 site; by taking a recombinant plasmid Yep352-PE as a template, PCR amplification was conducted by primer pairs PGK1p-U (SEQ ID NO:49) and PGK1t-D (SEQ ID NO:50) to obtain a PGK1p-Erg10-PGK1t segment with a strong promoter and a terminator; and by taking a pUG6 plasmid as a template, PCR amplification was conducted by primers KAN-U (SEQ ID NO:23) and KAN-D (SEQ ID NO:24) to obtain a selection marker KanMX.

Figure 4:
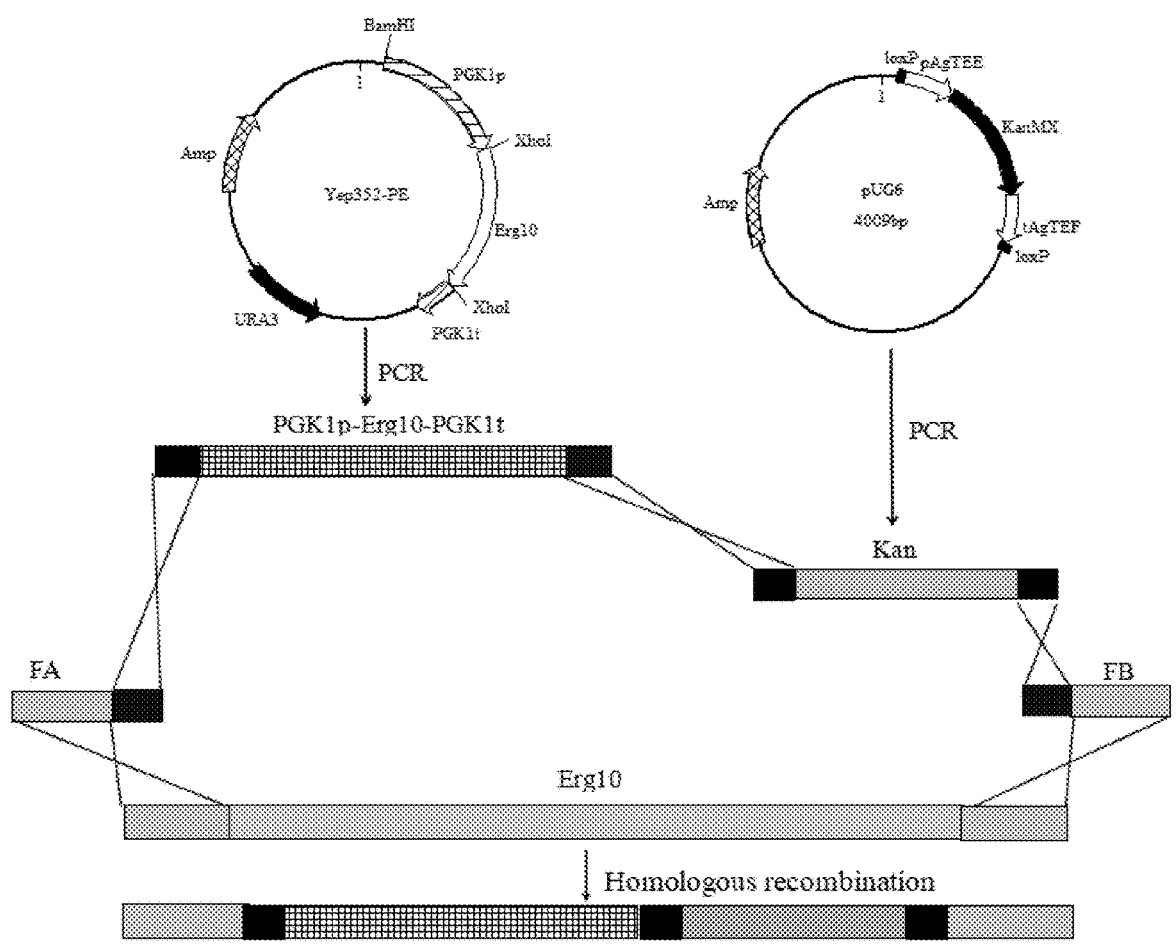
FIG. 4 is a schematic diagram of construction of a recombinant *Saccharomyces cerevisiae* strain overexpressing a gene Erg10 at Erg10.

By taking a *Saccharomyces cerevisiae* strain AY14-α as a starting strain and Erg10 as an integration site, the four segments Erg10-FA, Erg10-FB, PGK1p-Erg10-PGK1t and KanMX obtained by PCR were transformed into the a haploid obtained by raw spore separation of the *Saccharomyces cerevisiae* CICC32315 simultaneously by a lithium acetate transformation method, and were sequentially connected to and inserted into the integration site, and intracellular integration was conducted to obtain a *Saccharomyces cerevisiae* recombinant strain 1 after homologous recombination. The homologous recombination process diagram is shown in FIG. 4.

Figure 9A:
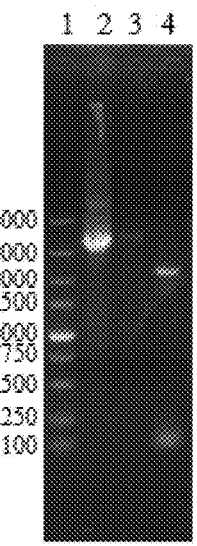
FIG. 9A is a verification electrophoretogram of construction of a strain, wherein lane 1 is a 5000 bp DNA Ladder Marker, lane 2 is a verification segment taking a recombinant strain genome as a template and Erg10-FA-U/Erg10-D as a primer, lane 3 is a verification segment taking a recombinant strain genome as a template and Erg10-U/KAN-D as a primer, and lane 4 is a verification segment taking a recombinant strain genome as a template and KAN-U/Erg10-FB-D as a primer.

Three groups of upstream and downstream primers were designed respectively according to the gene sequences at the two ends of the recombination site of the *Saccharomyces cerevisiae* CICC32315, and PCR amplification was conducted by taking a haploid transformant genome growing well as a template to verify a recombinant. The primer pairs Erg10-FA-U (SEQ ID NO:17) and Erg10-D (SEQ ID NO:22) served as upstream verification primers; the primer pairs Erg10-U (SEQ ID NO:21) and KAN-D (SEQ ID NO:24) served as midstream verification primers; and the primer pairs KAN-U (SEQ ID NO:23) and Erg10-FB-D (SEQ ID NO:20) served as downstream verification primers. A transformant verification agar gel electrophoretogram is shown in FIG. 9A, wherein lane 2 is an upstream verification band with a band size being about 3100 bp and consistent with the expectation, lane 3 is a midstream verification band with a band size being about 3300 bp and consistent with the expectation, and lane 4 is a downstream verification band with a band size being about 2100 bp and consistent with the expectation.

The plasmid pGAPza with Cre recombinant enzyme was transformed into the recombinant strain 1 by the lithium acetate transformation method to obtain a transformant; a monoclonal antibody was picked and induced in a galactose medium for 4 h to 5 h, dilution and coating was conducted, and a single colony was picked out onto a YPD plate and was photocopied on a G418 resistance plate; a strain capable of growing on the YPD plate and not growing on the G418 resistance plate was picked out and a genome was extracted to conduct PCR verification. The band of about 1600 bp cannot be obtained by amplifying the segment KanMX by taking the genome of the recombinant strain 1 as control, and the recombinant strain 1 can be amplified to obtain the segment, thus obtaining a recombinant strain 2 losing the selection marker KanMX. The recombinant strain 2 was inoculated into a YPD liquid culture medium for subculture and was transferred for once every 12 h, and the plasmid pGAPza may be lost after several generations, thus obtaining a recombinant strain 3 not containing the plasmid pGAPza.

② By taking the genome of the AY14-α as a template, PCR amplification was conducted by primer pairs AY14-α (SEQ ID NO:25) and GAL80-FA-D (SEQ ID NO:26) to obtain an upper homologous arm GAL80-FA of a GAL80 site; PCR amplification was conducted by primer pairs GAL80-FB-U (SEQ ID NO:27) and GAL80-FB-D (SEQ ID NO:28) to obtain a lower homologous arm GAL80-FB of the GAL80 site; by taking recombinant plasmids Yep352-PH and Yep352-PC as templates, PCR amplification was conducted respectively by primer pairs PGK1p-U (SEQ ID NO:49) and PGK1t-D (SEQ ID NO:50) to obtain PGK1p-Hbd-PGK1t and PGK1p-Crt-PGK1t segments with a strong promoter and a terminator; and by taking a pUG6 plasmid as a template, PCR amplification was conducted by primers KAN-U (SEQ ID NO:23) and KAN-D (SEQ ID NO:24) to obtain a selection marker KanMX.

Figure 5:
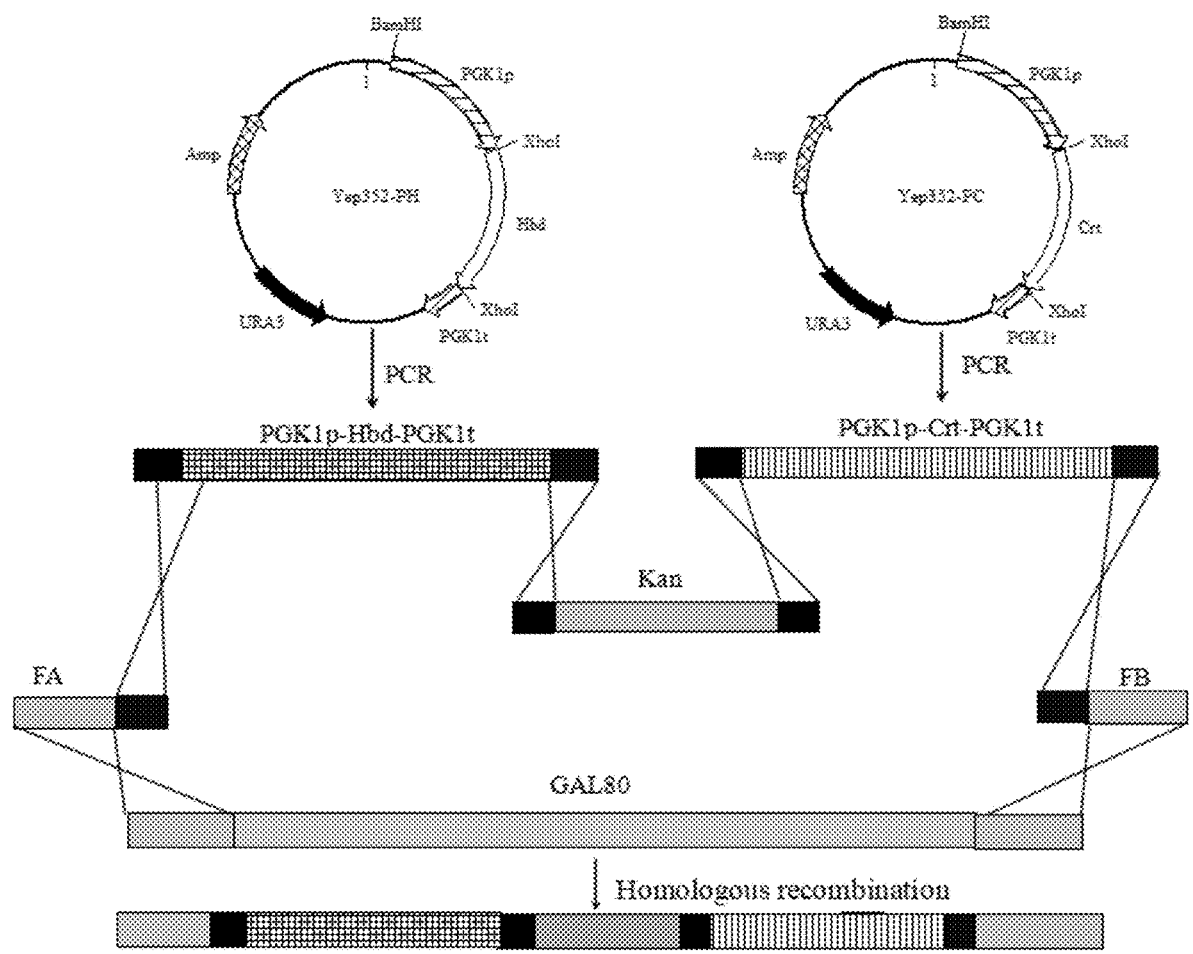
FIG. 5 is a schematic diagram of construction of a recombinant *Saccharomyces cerevisiae* strain overexpressing a gene Hbd and a gene Crt at GAL80.

By taking the gene GAL80 as an integration site, the five segments GAL80-FA, PGK1p-Hbd-PGK1t, PGK1p-Crt-PGK1t, KanMX and GAL80-FB obtained by PCR were transformed into the recombinant strain 3 simultaneously by the lithium acetate transformation method, and were sequentially connected to and inserted into the integration site, and intracellular integration was conducted to obtain a *Saccharomyces cerevisiae* recombinant strain 4 after homologous recombination. The homologous recombination process diagram is shown in FIG. 5.

Figure 9B:
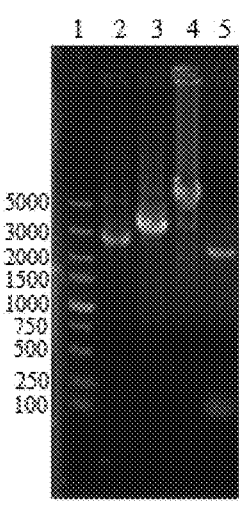
FIG. 9B is a verification electrophoretogram of construction of a strain, wherein lane 1 is a 5000 bp DNA Ladder Marker, lane 2 is a verification segment taking a recombinant strain genome as a template and HXT16-FA-U/Ter-D as a primer, lane 3 is a verification segment taking a recombinant strain genome as a template and Ter-U/KAN-D as a primer, lane 4 is a verification segment taking a recombinant strain genome as a template and KAN-U/AAT-D as a primer, and lane 5 is a verification segment taking a recombinant strain genome as a template and AAT-U/HXT16-FB-D as a primer.
Figure 9C:
FIG. 9C is a verification electrophoretogram of construction of a strain, wherein lane 1 is a 5000 bp DNA Ladder Marker, lane 2 is a verification segment taking a recombinant strain genome as a template and GAL80-FA-U/Hbd-D as a primer, lane 3 is a verification segment taking a recombinant strain genome as a template and Hbd-U/KAN-D as a primer, lane 4 is a verification segment taking a recombinant strain genome as a template and KAN-U/Crt-D as a primer, and lane 5 is a verification segment taking a recombinant strain genome as a template and Crt-U/GAL80-FB-D as a primer.

Four groups of verification were designed respectively according to the gene sequences at the two ends of the recombination site of the *Saccharomyces cerevisiae* CICC32315 and the inserted homologous recombination sequence, and PCR amplification was conducted by taking a haploid transformant genome growing well as a template to verify a recombinant. The primer pairs GAL80-FA-U (SEQ ID NO:25) and Hbd-D (SEQ ID NO:30) served as upstream verification primers; the primer pairs Hbd-U (SEQ ID NO:29) and KAN-D (SEQ ID NO:24) served as midstream verification primers; the primer pairs KAN-U (SEQ ID NO:23) and Crt-D (SEQ ID NO:32) served as midstream verification primers; and the primer pairs Crt-U (SEQ ID NO:31) and GAL80-FB-D (SEQ ID NO:28) served as downstream verification primers. A transformant verification agar gel electrophoretogram is shown in FIG. 9C, wherein lane 2 is an upstream verification band with a band size being about 2700 bp and consistent with the expectation, lane 3 is a midstream verification band with a band size being about 3000 bp and consistent with the expectation, lane 4 is a midstream verification band with a band size being about 5000 bp and consistent with the expectation, and lane 5 is a midstream verification band with a band size being about 1500 bp and consistent with the expectation.

The plasmid pGAPza with Cre recombinant enzyme was transformed into the recombinant strain 4 by the lithium acetate transformation method to obtain a transformant; a monoclonal antibody was picked and induced in a galactose medium for 4 h to 5 h, dilution and coating was conducted, and a single colony was picked out onto a YPD plate and was photocopied on a G418 resistance plate; a strain capable of growing on the YPD plate and not growing on the G418 resistance plate was picked out and a genome was extracted to conduct PCR verification. The band of about 1600 bp cannot be obtained by amplifying the segment KanMX by taking the genome of the recombinant strain 4 as control, and the recombinant strain 4 can be amplified to obtain the segment, thus obtaining a recombinant strain 5 losing the selection marker KanMX. The recombinant strain 5 was inoculated into a YPD liquid culture medium for subculture and was transferred for once every 12 h, and the plasmid pGAPza may be lost after several generations, thus obtaining a recombinant strain 6 not containing the plasmid pGAPza.

③ By taking the genome of the AY14-α as a template, PCR amplification was conducted by primer pairs HXT16-FA-U (SEQ ID NO:33) and HXT16-FA-D (SEQ ID NO:34) to obtain an upper homologous arm HXT16-FA of a HXT16 site; PCR amplification was conducted by primer pairs HXT16-FB-U (SEQ ID NO:35) and HXT16-FB-D (SEQ ID NO:36) to obtain a lower homologous arm HXT16-FB of the HXT16 site; by taking recombinant plasmids Yep352-PT and Yep352-PA as templates, PCR amplification was conducted respectively by primer pairs PGK1p-U (SEQ ID NO:49) and PGK1t-D (SEQ ID NO:50) to obtain PGK1p-Ter-PGK1t and PGK1p-AAT-PGK1t segments with a strong promoter and a terminator; and by taking a pUG6 plasmid as a template, PCR amplification was conducted by primers KAN-U (SEQ ID NO:23) and KAN-D (SEQ ID NO:24) to obtain a selection marker KanMX.

Figure 6:
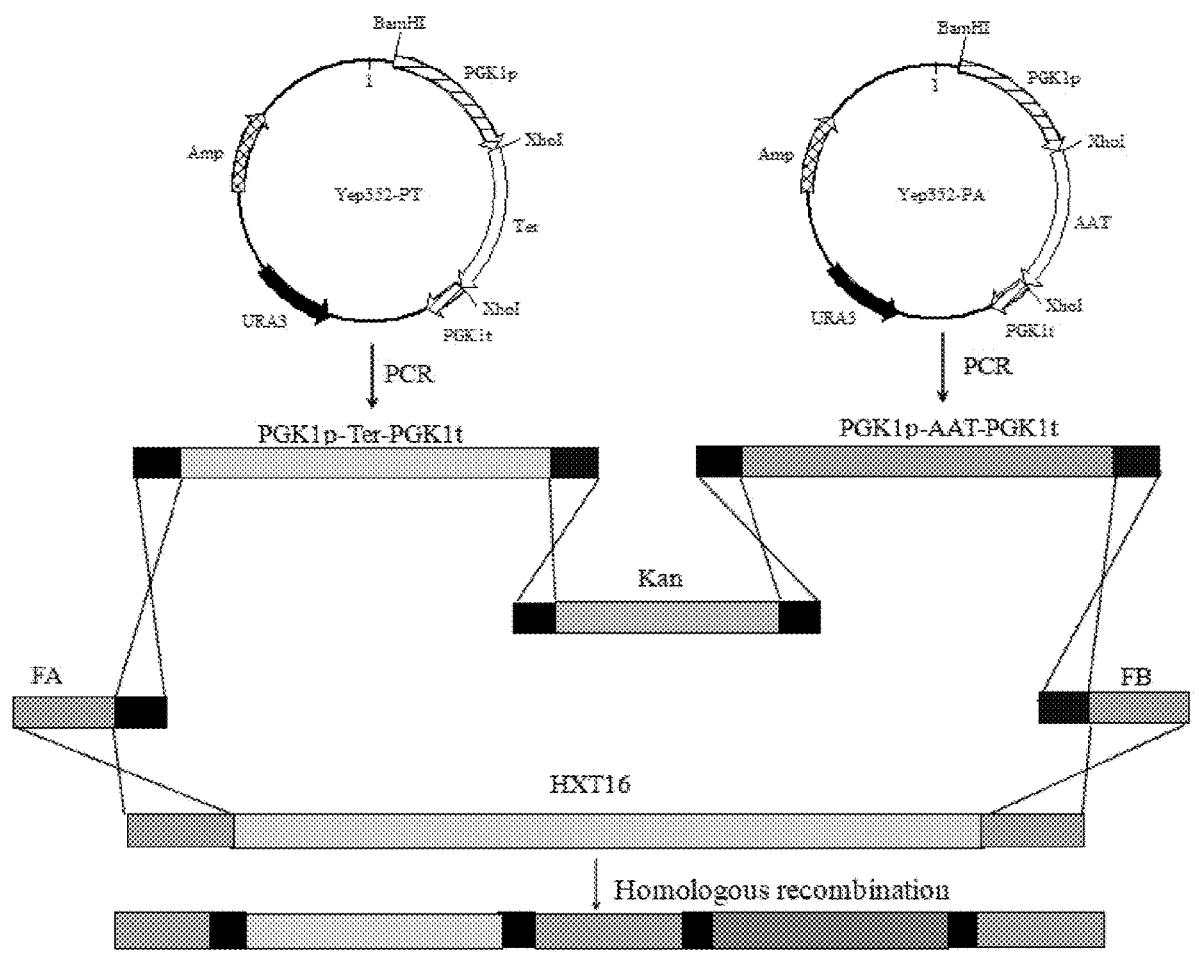
FIG. 6 is a schematic diagram of construction of a recombinant *Saccharomyces cerevisiae* strain overexpressing a gene Ter and a gene AAT at HXT16.

By taking the gene HXT16 as an integration site, the five segments HXT16-FA, PGK1p-Ter-PGK1t, PGK1p-AAT-PGK1t, KanMX and HXT16-FB obtained by PCR were transformed into the recombinant strain 6 simultaneously by the lithium acetate transformation method, and were sequentially connected to and inserted into the integration site, and intracellular integration was conducted to obtain a *Saccharomyces cerevisiae* recombinant strain 7 after homologous recombination. The homologous recombination process diagram is shown in FIG. 6.

Four groups of verification were designed respectively according to the gene sequences at the two ends of the recombination site of the *Saccharomyces cerevisiae* CICC32315 and the inserted homologous recombination sequence, and PCR amplification was conducted by taking a haploid transformant genome growing well as a template to verify a recombinant. The primer pairs HXT16-FA-U (SEQ ID NO:33) and Ter-D (SEQ ID NO:38) served as upstream verification primers; the primer pairs Ter-U (SEQ ID NO:37) and KAN-D (SEQ ID NO:24) served as midstream verification primers; the primer pairs KAN-U (SEQ ID NO:23) and AAT-D (SEQ ID NO:40) served as midstream verification primers; and the primer pairs AAT-U (SEQ ID NO:39) and HXT16-FB-D (SEQ ID NO:36) served as downstream verification primers. A transformant verification agar gel electrophoretogram is shown in FIG. 9B, wherein lane 2 is an upstream verification band with a band size being about 2700 bp and consistent with the expectation, lane 3 is a midstream verification band with a band size being about 3000 bp and consistent with the expectation, lane 4 is a midstream verification band with a band size being about 5100 bp and consistent with the expectation, and lane 5 is a midstream verification band with a band size being about 2100 bp and consistent with the expectation.

The plasmid pGAPza with Cre recombinant enzyme was transformed into the recombinant strain 7 by the lithium acetate transformation method to obtain a transformant; a monoclonal antibody was picked and induced in a galactose medium for 4 h to 5 h, dilution and coating was conducted, and a single colony was picked out onto a YPD plate and was photocopied on a G418 resistance plate; a strain capable of growing on the YPD plate and not growing on the G418 resistance plate was picked out and a genome was extracted to conduct PCR verification. The band of about 1600 bp cannot be obtained by amplifying the segment KanMX by taking the genome of the recombinant strain 7 as control, and the recombinant strain 7 can be amplified to obtain the segment, thus obtaining a recombinant strain 8 losing the selection marker KanMX. The recombinant strain 8 was inoculated into the YPD liquid culture medium for subculture and was transferred for once every 12 h, and the plasmid pGAPza may be lost after several generations, thus obtaining a recombinant strain 9 not containing the plasmid pGAPza (that is, obtaining a *Saccharomyces* strain EST).

(4) Singly Double-Copying the Gene Ter

By taking the genome of the AY14-α as a template, PCR amplification was conducted by primer pairs LPP1-FA-U (SEQ ID NO:41) and LPP1-FA-D (SEQ ID NO:42) to obtain an upper homologous arm LPP1-FA of a LPP1 site; PCR amplification was conducted by primer pairs LPP1-FB-U (SEQ ID NO:43) and LPP1-FB-D (SEQ ID NO:44) to obtain a lower homologous arm LPP1-FB of the LPP1 site; by taking the recombinant plasmid Yep352-PE as a template, PCR amplification was conducted by primer pairs PGK1p-U (SEQ ID NO:49) and PGK1t-D (SEQ ID NO:50) to obtain a PGK1p-Ter-PGK1t segment with a strong promoter and a terminator; and by taking a pUG6 plasmid as a template, PCR amplification was conducted by primers KAN-U (SEQ ID NO:23) and KAN-D (SEQ ID NO:24) to obtain a selection marker KanMX.

Figure 7:
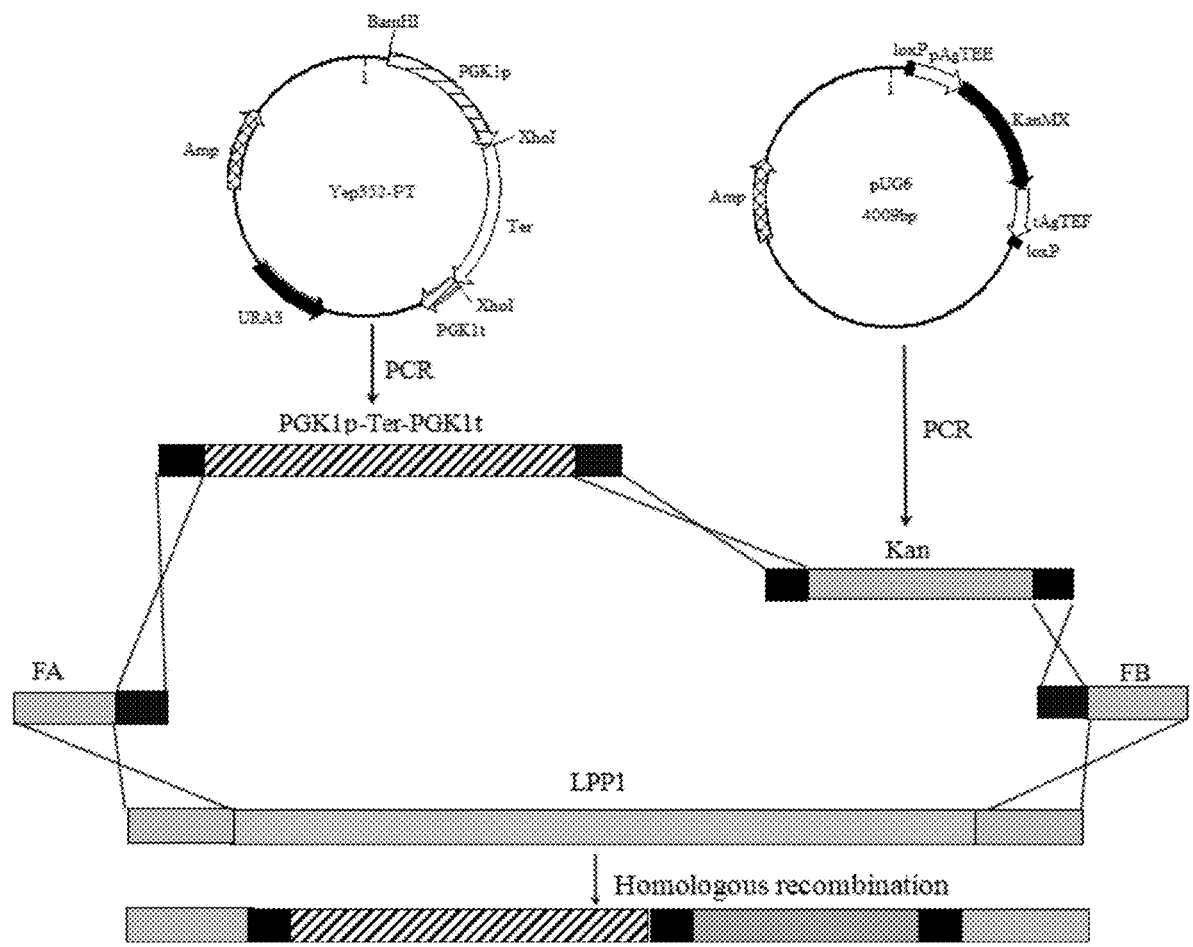
FIG. 7 is a schematic diagram of construction of a recombinant *Saccharomyces cerevisiae* strain performing double-copy on a gene Ter at LPP1.

By taking the gene LPP1 as an integration site, the four segments LPP1-FA, PGK1p-Ter-PGK1t, KanMX and LPP1-FB obtained by PCR were transformed into the recombinant strain 9 simultaneously by the lithium acetate transformation method, and were sequentially connected to and inserted into the integration site, and intracellular integration was conducted to obtain a *Saccharomyces cerevisiae* recombinant strain 10 after homologous recombination. The homologous recombination process diagram is shown in FIG. 7.

Figure 9D:
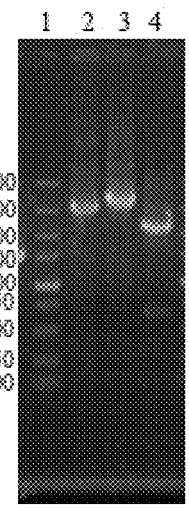
FIG. 9D lane 1 is a 5000 bp DNA Ladder Marker, lane 2 is a verification segment taking a recombinant strain genome as a template and LPP1-FA-U/Ter-D as a primer, lane 3 is a verification segment taking a recombinant strain genome as a template and Ter-U/KAN-D as a primer, and lane 4 is a verification segment taking a recombinant strain genome as a template and KAN-U/LPP1-FB-D as a primer.

Three groups of verification were designed respectively according to the gene sequences at the two ends of the recombination site of the *Saccharomyces cerevisiae* CICC32315 and the inserted homologous recombination sequence, and PCR amplification was conducted by taking a haploid transformant genome growing well as a template to verify a recombinant. The primer pairs LPP1-FA-U (SEQ ID NO:41) and Ter-D (SEQ ID NO:38) served as upstream verification primers; the primer pairs Ter-U (SEQ ID NO:37) and KAN-D (SEQ ID NO:24) served as midstream verification primers; and the primer pairs KAN-U (SEQ ID NO:23) and LPP1-FB-D (SEQ ID NO:44) served as downstream verification primers. A transformant verification agar gel electrophoretogram is shown in FIG. 9D, wherein lane 2 is an upstream verification band with a band size being about 3000 bp and consistent with the expectation, lane 3 is a midstream verification band with a band size being about 3100 bp and consistent with the expectation, and lane 4 is a downstream verification band with a band size being about 2100 bp and consistent with the expectation.

The plasmid pGAPza with Cre recombinant enzyme was transformed into the recombinant strain 10 by the lithium acetate transformation method to obtain a transformant; a monoclonal antibody was picked and induced in a galactose medium for 4 h to 5 h, dilution and coating was conducted, and a single colony was picked out onto a YPD plate and was photocopied on a G418 resistance plate; a strain capable of growing on the YPD plate and not growing on the G418 resistance plate was picked out and a genome was extracted to conduct PCR verification. The band of about 1600 bp cannot be obtained by amplifying the segment KanMX by taking the genome of the recombinant strain 10 as control, and the recombinant strain 10 can be amplified to obtain the segment, thus obtaining a recombinant strain 11 losing the selection marker KanMX. The recombinant strain 11 was inoculated into the YPD liquid culture medium for subculture and was transferred for once every 12 h, and the plasmid pGAPza may be lost after several generations, thus obtaining a recombinant strain 12 not containing the plasmid pGAPza. (That is, obtaining a *Saccharomyces* strain EDT)

(4) Singly Double-Copying the Gene AAT

By taking the genome of the AY14-α as a template, PCR amplification was conducted by primer pairs KU70-FA-U (SEQ ID NO:45) and KU70-FA-D (SEQ ID NO:46) to obtain an upper homologous arm KU70-FA of a KU70 site; PCR amplification was conducted by primer pairs KU70-FB-U (SEQ ID NO:47) and KU70-FB-D (SEQ ID NO:48) to obtain a lower homologous arm KU70-FB of the KU70 site; by taking the recombinant plasmid Yep352-PA as a template, PCR amplification was conducted by primer pairs PGK1p-U (SEQ ID NO:49) and PGK1t-D (SEQ ID NO:50) to obtain a PGK1p-AAT-PGK1t segment with a strong promoter and a terminator; and by taking a pUG6 plasmid as a template, PCR amplification was conducted by primers KAN-U (SEQ ID NO:23) and KAN-D (SEQ ID NO:24) to obtain a selection marker KanMX.

Figure 8:
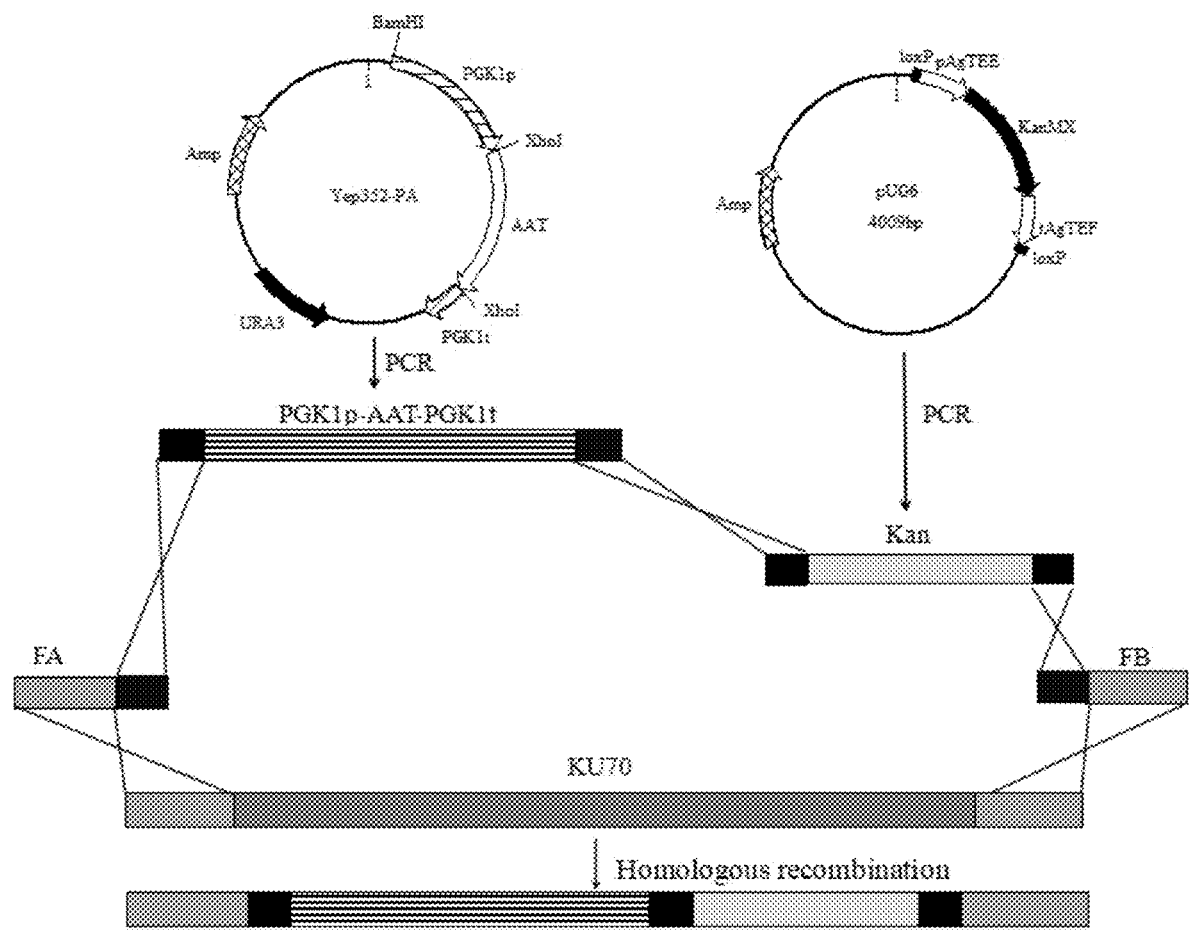
FIG. 8 is a schematic diagram of construction of a recombinant *Saccharomyces cerevisiae* strain performing double-copy on a gene AAT at KU70.

By taking the gene KU70 as an integration site, the four segments KU70-FA, PGK1p-AAT-PGK1t, KanMX and KU70-FB obtained by PCR were transformed into the recombinant strain 9 simultaneously by the lithium acetate transformation method, and were sequentially connected to and inserted into the integration site, and intracellular integration was conducted to obtain a *Saccharomyces cerevisiae* recombinant strain 13 after homologous recombination. The homologous recombination process diagram is shown in FIG. 8.

Figure 9E:
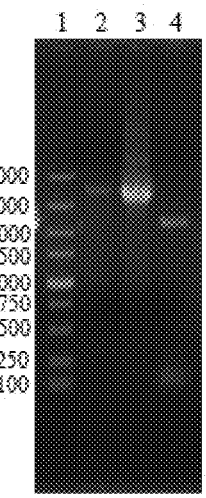
FIG. 9E is a verification electrophoretogram of construction of a strain, wherein lane 1 is a 5000 bp DNA Ladder Marker, lane 2 is a verification segment taking a recombinant strain genome as a template and KU70-FA-U/AAT-D as a primer, lane 3 is a verification segment taking a recombinant strain genome as a template and AAT-U/KAN-D as a primer, and lane 4 is a verification segment taking a recombinant strain genome as a template and KAN-U/KU70-FB-D as a primer.

Four groups of verification were designed respectively according to the gene sequences at the two ends of the recombination site of the *Saccharomyces cerevisiae* CICC32315 and the inserted homologous recombination sequence, and PCR amplification was conducted by taking a haploid transformant genome growing well as a template to verify a recombinant. The primer pairs KU70-FA-U (SEQ ID NO:45) and AAT-D (SEQ ID NO:40) served as upstream verification primers; the primer pairs AAT-U (SEQ ID NO:39) and KAN-D (SEQ ID NO:24) served as midstream verification primers; and the primer pairs KAN-U (SEQ ID NO:23) and KU70-FB-D (SEQ ID NO:48) served as downstream verification primers. A transformant verification agar gel electrophoretogram is shown in FIG. 9E, wherein lane 2 is an upstream verification band with a band size being about 3300 bp and consistent with the expectation, lane 3 is a midstream verification band with a band size being about 3100 bp and consistent with the expectation, and lane 4 is a downstream verification band with a band size being about 2100 bp and consistent with the expectation. (That is, obtaining a strain EDS)

(5) Double-Copying the Gene Ter and the Gene AAT Simultaneously

By taking the gene KU70 as an insertion site, the four segments KU70-FA, PGK1p-AAT-PGK1t, KanMX and KU70-FB (the segment obtaining method is as same as the method of singly double-copying the gene AAT in (4)) obtained by PCR were transformed into the recombinant strain 12 (the strain prepared by (3) singly double-copying the gene Ter) simultaneously, and were sequentially connected to and inserted into the integration site, and intracellular integration was conducted to obtain a *Saccharomyces cerevisiae* recombinant strain 14 after homologous recombination. The homologous recombination process diagram is shown in FIG. 8.

Figure 9F:
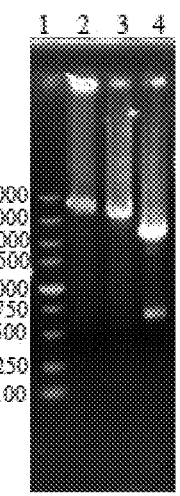
FIG. 9F is a verification electrophoretogram of construction of a strain, wherein lane 1 is a 5000 bp DNA Ladder Marker, lane 2 is a verification segment taking a recombinant strain genome as a template and KU70-FA-U/AAT-D as a primer, lane 3 is a verification segment taking a recombinant strain genome as a template and AAT-U/KAN-D as a primer, and lane 4 is a verification segment taking a recombinant strain genome as a template and KAN-U/KU70-FB-D as a primer.

Four groups of verification were designed respectively according to the gene sequences at the two ends of the recombination site of the *Saccharomyces cerevisiae* CICC32315 and the inserted homologous recombination sequence, and PCR amplification was conducted by taking a haploid transformant genome growing well as a template to verify a recombinant. The primer pairs KU70-FA-U (SEQ ID NO:45) and AAT-D (SEQ ID NO:40) served as upstream verification primers; the primer pairs AAT-U (SEQ ID NO:39) and KAN-D (SEQ ID NO:24) served as midstream verification primers; and the primer pairs KAN-U (SEQ ID NO:23) and KU70-FB-D (SEQ ID NO:48) served as downstream verification primers. A transformant verification agar gel electrophoretogram is shown in FIG. 9F, wherein lane 2 is an upstream verification band with a band size being about 3300 bp and consistent with the expectation, lane 3 is a midstream verification band with a band size being about 3100 bp and consistent with the expectation, and lane 4 is a downstream verification band with a band size being about 2100 bp and consistent with the expectation. That is, obtaining a strain EDS.

Embodiment 2: Corn Raw Material Thick Mash Fermentation Experiment of Starting Strain and Modified Strain (1) corn raw material thick mash fermentation experiment of the recombinant strains EST, EDT, EDS and EDST, and the parent strain (AY14-α)

The parent strain AY14-α, and the recombinant strains EST, EDT, EDS and EDST were subjected to corn raw material thick mash fermentation experiments respectively, the fermentation process route diagram: corn flour→soaking→liquification→saccharification→cooling→inoculation→fermentation→wine steaming→index measurement; and one ring of saccharomyces cells were picked respectively, inoculated into a test tube filled with 5 mL of primary seed culture medium respectively for static culture at 30° C. for 24 h, inoculated into a 150 mL triangular flask filled with 45 mL of secondary seed culture medium according to 10% of inoculation amount for static culture at 30° C. for 16 h until the later stage of a logarithmic phase, and inoculated into a fermentation medium according to 10% of inoculation amount for static culture at 30° C. Weighing was conducted for one time every 12 h, and fermentation ended when the weight loss of two times was less than 1 g, that is, fermentation ended after 84 h fermentation. After fermentation, 100 mL of water was added to 100 mL of mash to steam 100 mL of wine sample. The fermentation performance indexes such as $CO_2$ cumulative emission, alcoholic strength, residual reducing sugar and the like were measured. The result is shown in Table 3.

The primary seed culture medium consists of corn flour of 82 g/L, high-temperature resistant α-amylase with an adding amount being about $1.0 \times 10^4$ U/L, saccharifying enzyme with enzyme activity being about –35 U/L and the balance of water, the sugar degree being 8° BX.

The primary seed culture medium consists of corn flour of 125 g/L, high-temperature resistant α-amylase with an adding amount being about $1.5 \times 10^4$ U/L, saccharifying enzyme with enzyme activity being about 50 U/L and the balance of water, the sugar degree being 12° BX.

The fermentation medium consists of corn flour of 315 g/L, high-temperature resistant α-amylase of $3.5 \times 10^4$ U/L, saccharifying enzyme of 95 U/L, acid proteinase of 15 U/L, nutritive salt solution of 5.5-5.6 mL/L and the balance of water, wherein the nutritive salt solution consists of $MgSO_4$ of 150 g/L, $KH_2PO_4$ of 75 g/L, urea of 81 g/L and the balance of water, and is stored at 4° C. after being filtered.

The treatment process condition of the fermentation medium is as follows:

soaking condition: soaking the corn flour at 60° C. to 70° C. for 20 min; liquefying condition: at 85° C. to 90° C., adding the high-temperature resistant α-amylase according to the above proportion and liquefying for 90 min; and saccharifying condition: at 55° C. to 60° C., adding the saccharifying enzyme, saccharifying for 20 min, adding the nutritive salt solution and the acid proteinase, reacting at 30° C. for 20 min to obtain the fermentation medium.

Table 3 Comparison of Fermentation Performance between Parent Strain and Recombinant

TABLE 3

Comparison of Fermentation Performance between Parent Strain and Recombinant Strain

| Strain | 20° C. Standard Alcohol Strength (% vol) | Residual Sugar (g/100 mL) | $CO_2$ Weight Loss (g) |
|---|---|---|---|
| AY14-α | 16.23 ± 0.41 | 0.23 ± 0.01 | 23.49 ± 0.89 |
| EST | 15.94 ± 0.37 | 0.40 ± 0.03 | 23.61 ± 0.94 |
| EDT | 15.70 ± 0.44 | 0.35 ± 0.01 | 23.81 ± 0.49 |
| EDS | 16.37 ± 0.51 | 0.23 ± 0.03 | 23.58 ± 1.13 |
| EDST | 16.53 ± 0.45 | 0.21 ± 0.01 | 23.97 ± 0.76 |

Note:
the data shown is the average value of three parallel experimental results.

Figure 10:
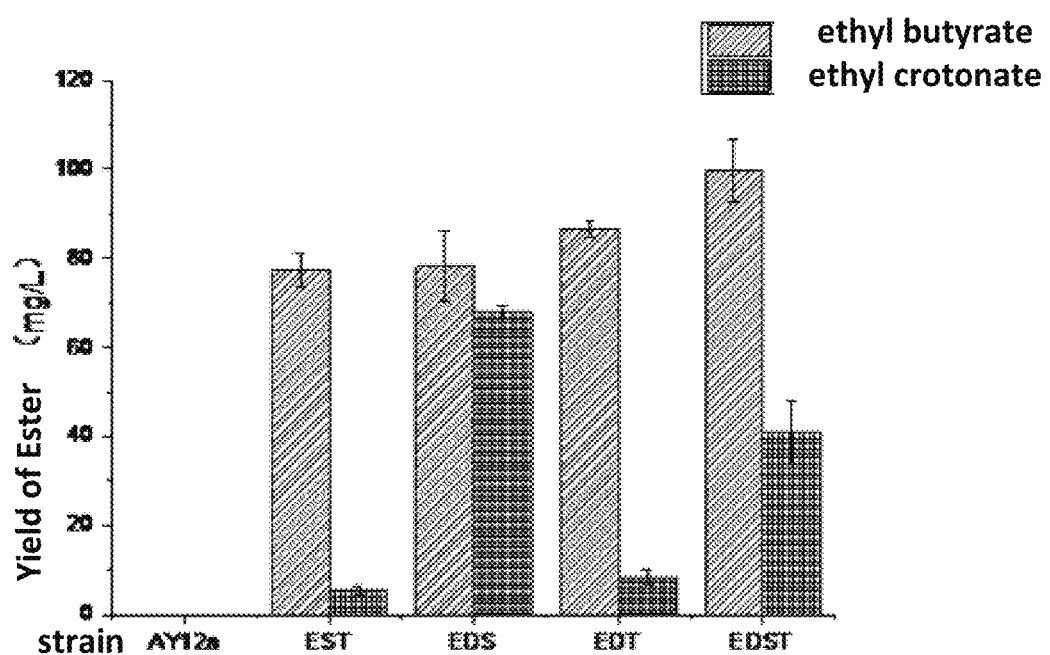
FIG. 10 is a diagram showing experimental results of yield of ethyl butyrate and ethyl crotonate of a parent strain and a *Saccharomyces cerevisiae* modified strain in each stage.

Referring to Table 3 and FIG. 10, it can be seen that the alcohol content and the residual sugar content of the fermented recombinant strains EST, EDT, EDS and EDST are not significantly different from those of the starting strain AY14-α, which indicates that the growth and fermentation performance of the modified strain do not change significantly.

(2) Yield of Ester Measured by GC-MS

For the 100 mL of wine sample finally obtained from the corn raw material thick mash fermentation experiment of the recombinant strains EST, EDT, EDS and EDST and the parent strain (AY14-α) mentioned in (1), the yield of the ethyl butyrate and the yield of the ethyl crotonate were measured.

Measurement method: setting the GC condition of a gaschromatograph: chromatographic column HP-SMS, and 60 m×0.32 mm×0.25 μm quartz capillary column; the temperature of a sample inlet is 250° C.; the carrier gas is high-purity helium with a flow speed of 1 mL/min; the column temperature starts at 40° C. for 3 min, rises to 116° C. at 9/min ° C. for 4 min, then rises to 260° C. at 9/min ° C. for 5 min; and splitless sample injection. The mass spectrometer condition: the ion source is an EI source, the temperature of the ion source is 230° C., electronic energy is 70 eV, the temperature of a quadrupole rod is 150° C., the interface temperature is 280° C., the voltage of an electron multiplier is 1280 V, and the scanning range m/z is 40 u to 450 u.

The measured yields of the ethyl butyrate and the ethyl crotonate of the recombinant strains EST, EDT, EDS and EDST and the parent strain (AY14-α) are shown in Table 4.

Table 4 Ester Yield of Parent Strain and Recombinant Strains (unit: mg/L)

TABLE 4

Ester Yield of Parent Strain and Recombinant Strains (unit: mg/L)

| Strain | AY14-α | EST | EDT | EDS | EDST |
|---|---|---|---|---|---|
| Ethyl butyrate (mg/L) | NF | 77.33 ± 3.79 | 86.6 ± 2.03 | 78.16 ± 5.31 | 99.65 ± 7.32 |
| Ethyl crotonate (mg/L) | NF | 1.49 ± 0.37 | 8.38 ± 1.04 | 68.01 ± 1.01 | 40.93 ± 3.18 |

Note:
the data shown is the average value of three parallel experimental results.

In Table 3 and Table 4, the AY14-α is the original strain, the EST is the strains of the overexpressed genes Erg10, Hbd, Crt, Ter and AAT, the EDS is the strain only double-copying AAT based on the EST, the EDT is the strain only double-copying Ter based on the EST, and the EDST is the strain double-copying AAT and Ter based on the EST.

What is claimed is:

1. A genetically engineered *Saccharomyces cerevisiae* strain for producing ethyl butyrate, wherein the genetically engineered *Saccharomyces cerevisiae* strain is obtained by using *Saccharomyces cerevisiae* as an original strain and over-expressing acetyl-CoA C-acetyltransferase gene Erg10, 3-hydroxybutyryl-CoA dehydrogenase gene Hbd, 3-hydroxybutyryl-CoA dehydratase gene Crt, trans-2-enoyl-CoA reductase gene Ter and alcohol acyltransferase gene AAT;
   wherein the acetyl-CoA C-acetyltransferase gene Erg10 is overexpressed by a first strong promoter;
   wherein the 3-hydroxybutyryl-CoA dehydrogenase gene Hbd and the 3-hydroxybutyryl-CoA dehydratase gene Crt are arranged in tandem together to replace gene GAL80 and the 3-hydroxybutyryl-CoA dehydrogenase gene Hbd and the 3-hydroxybutyryl-CoA dehydratase gene Crt are both overexpressed by a second strong promoter;
   wherein the trans-2-enoyl-CoA reductase gene Ter and the alcohol acyltransferase gene AAT are arranged in tandem together to replace gene HXT16 and the trans-2-enoyl-CoA reductase gene Ter and the alcohol acyltransferase gene AAT are both overexpressed by a third strong promoter; and
   wherein ethyl butyrate production of the genetically engineered *Saccharomyces cerevisiae* strain is improved relative to the original strain.

2. The genetically engineered *Saccharomyces cerevisiae* strain according to claim 1, wherein at least one of the trans-2-enoyl-CoA reductase gene Ter and the alcohol acyltransferase gene AAT is dual-copy expressed.

3. The genetically engineered *Saccharomyces cerevisiae* strain according to claim 1, wherein
   the nucleotide sequence of the acetyl-CoA C-acetyltransferase gene Erg10 is as shown by SEQ ID NO:1;
   the nucleotide sequence of the 3-hydroxybutyryl-CoA dehydrogenase gene Hbd is as shown by SEQ ID NO:2;
   the nucleotide sequence of the 3-hydroxybutyryl-CoA dehydratase gene Crt is as shown by SEQ ID NO:3;
   the nucleotide sequence of the trans-2-enoyl-CoA reductase gene Ter is as shown by SEQ ID NO:4; and
   the nucleotide sequence of the alcohol acyltransferase gene AAT is as shown by SEQ ID NO:5.

4. The genetically engineered *Saccharomyces cerevisiae* strain according to claim 1, wherein the original strain is *Saccharomyces cerevisiae* CICC32315.

5. The genetically engineered *Saccharomyces cerevisiae* strain according to claim 1, wherein the trans-2-enoyl-CoA reductase gene Ter is dual-copy expressed by further replacing gene LPP1 and overexpressing by a fourth strong promoter or the alcohol acyltransferase gene AAT is dual-copy expressed by further replacing gene KU70 and overexpressing by a fourth strong promoter.

6. The genetically engineered *Saccharomyces cerevisiae* strain according to claim 5, wherein the trans-2-enoyl-CoA reductase gene Ter is dual-copy expressed by replacing gene LPP1 and overexpressing by the fourth strong promoter.

7. The genetically engineered *Saccharomyces cerevisiae* strain according to claim 5, wherein the alcohol acyltransferase gene AAT is dual-copy expressed by replacing gene KU70 and overexpressing by the fourth strong promoter.

8. The genetically engineered *Saccharomyces cerevisiae* strain according to claim 1, wherein the first, second, and third strong promoters are PGK1$_P$.

9. A method of using the genetically engineered *Saccharomyces cerevisiae* strain according to claim 1 to produce ethyl butyrate, comprising culturing the genetically engineered *Saccharomyces cerevisiae* strain in a fermentation medium to produce ethyl butyrate.

10. The method according to claim 9, wherein the culturing comprises performing a two-stage activation of the genetically engineered *Saccharomyces cerevisiae* strain to produce a seed solution, inoculating the seed solution with a 8-12% inoculation amount to the fermentation medium, and then standing the fermentation medium for a fermentation for 80-86 h at 28-30° C.; wherein components of the fermentation medium comprise 300-320 g/L of corn flour, $2 \times 10^4$ to $5 \times 10^4$ U/L of a heat-resisting α-amylase, 90-100 U/L of a glucoamylase, 10-20 U/L of an acid proteinase, 5.5-5.6 mL/L of a nutritive salt solution and water as balance; and the nutritive salt solution comprises 140-160 g/L of $MgSO_4$, 70-80 g/L of $KH_2PO_4$, 80-85 g/L of carbamide and water as balance.

11. The method according to claim 9, wherein at least one of the trans-2-enoyl-CoA reductase gene Ter and the alcohol acyltransferase gene AAT is dual-copy expressed.

12. The method according to claim 9, wherein
   the nucleotide sequence of the acetyl-CoA C-acetyltransferase gene Erg10 is as shown by SEQ ID NO:1;
   the nucleotide sequence of the 3-hydroxybutyryl-CoA dehydrogenase gene Hbd is as shown by SEQ ID NO:2;
   the nucleotide sequence of the 3-hydroxybutyryl-CoA dehydratase gene Crt is as shown by SEQ ID NO:3;
   the nucleotide sequence of the trans-2-enoyl-CoA reductase gene Ter is as shown by SEQ ID NO:4; and
   the nucleotide sequence of the alcohol acyltransferase gene AAT is as shown by SEQ ID NO:5.

13. The method according to claim 9, wherein the original strain is *Saccharomyces cerevisiae* CICC32315.

14. The method according to claim 9, wherein the trans-2-enoyl-CoA reductase gene Ter is dual-copy expressed by further replacing gene LPP1 and overexpressing by a fourth strong promoter or the alcohol acyltransferase gene AAT is dual-copy expressed by further replacing gene KU70 and overexpressing by a fourth strong promoter.

15. The method according to claim 14, wherein the first, second, third, and fourth strong promoters are $PGK1_P$.

* * * * *